US012571728B2

(12) United States Patent
Högblom

(10) Patent No.: US 12,571,728 B2
(45) Date of Patent: Mar. 10, 2026

(54) METHOD FOR DETECTING A LIQUID COMPOSITION APPLIED ONTO A CELLULOSE BLANK STRUCTURE WITH A DETECTION SYSTEM AND A DETECTION SYSTEM

(71) Applicant: PulPac AB, Västra Frölunda (SE)

(72) Inventor: Olle Högblom, Gothenburg (SE)

(73) Assignee: PulPac AB, Västra Frölunda (SE)

( * ) Notice: Subject to any disclaimer, the term of this patent is extended or adjusted under 35 U.S.C. 154(b) by 166 days.

(21) Appl. No.: 18/565,320

(22) PCT Filed: Jun. 8, 2022

(86) PCT No.: PCT/EP2022/065551
§ 371 (c)(1),
(2) Date: Nov. 29, 2023

(87) PCT Pub. No.: WO2022/258688
PCT Pub. Date: Dec. 15, 2022

(65) Prior Publication Data
US 2024/0255422 A1     Aug. 1, 2024

(30) Foreign Application Priority Data

Jun. 11, 2021     (EP) ..................................... 21179093

(51) Int. Cl.
*G01N 21/3577*     (2014.01)
*B01L 3/00*     (2006.01)
(Continued)

(52) U.S. Cl.
CPC ........ *G01N 21/3577* (2013.01); *B01L 3/5023* (2013.01); *G01J 5/0037* (2013.01);
(Continued)

(58) Field of Classification Search
CPC .......................... G01N 21/3577; G01N 33/34; G01N 33/343; B01L 3/5023; B01L 2300/0663;
(Continued)

(56) References Cited

U.S. PATENT DOCUMENTS 5,338,361 A * 8/1994 Anderson ................ G05D 5/03
                                                        118/688
2009/0126889 A1   5/2009 Thomas et al.
2019/0120779 A1*  4/2019 Vonderheiden ...... G01N 33/346

FOREIGN PATENT DOCUMENTS

KR        101284351 B1 * 7/2013 ............... D06B 1/02
SE          1750313 A1 * 9/2018 ............. B65B 43/12
WO   WO-2021/001276 A1   1/2021

OTHER PUBLICATIONS

European Search Report, European Application No. 21179093.6, dated Nov. 9, 2021.

(Continued)

*Primary Examiner* — Kara E. Geisel
*Assistant Examiner* — Christina I Xing
(74) *Attorney, Agent, or Firm* — Sage Patent Group

(57) ABSTRACT

A method for detecting a liquid composition applied onto a cellulose blank structure, with a detection system. The detection system forms part of a cellulose product forming unit for forming cellulose products from the cellulose blank structure. The detection system includes a detection unit connected to a control unit. The method includes: providing the cellulose blank structure and feeding the cellulose blank structure in a feeding direction, where the cellulose blank structure moves through an application area and a detection area, the application area being arranged upstream the detection area; applying the liquid composition onto the cellulose blank structure in the application area; detecting the applied liquid composition in the detection area with the detection unit; analysing a detection result formed by the (Continued)

detection by the control unit, thereby forming an analysis result; and initiating a control action by the control unit upon detection of an analysis result deviating from a pre-determined analysis result.

14 Claims, 10 Drawing Sheets

(51) Int. Cl.
    *G01J 5/00*         (2022.01)
    *G16C 20/20*     (2019.01)
(52) U.S. Cl.
    CPC ...... *G16C 20/20* (2019.02); *B01L 2300/0663* (2013.01); *B01L 2300/126* (2013.01)
(58) Field of Classification Search
    CPC ........... B01L 2300/126; B31B 2110/20; B31B 50/006; B31B 50/142; B31B 50/592; B31B 50/747; G01J 5/0037; G16C 20/20
    See application file for complete search history.

(56)            References Cited

OTHER PUBLICATIONS

International Search Report and Written Opinion, International Application No. PCT/EP2022/065551, mailed Aug. 22, 2022.

* cited by examiner $R_{APD}, I_{REF}$ $T_{PD}, TM_{PD}$ $R_A, I$ $T_D = T_{PD}$ $TM = TM_{PD}$ $R_A, I$ $T_D$          $T_D$ $TM \neq TM_{PD}$          $T_1$    $T_2$    $T_3$

1

METHOD FOR DETECTING A LIQUID COMPOSITION APPLIED ONTO A CELLULOSE BLANK STRUCTURE WITH A DETECTION SYSTEM AND A DETECTION SYSTEM

TECHNICAL INVENTION

The present disclosure relates to a method for detecting a liquid composition applied onto a cellulose blank structure with a detection system. The disclosure further relates to a detection system for detecting a liquid composition applied onto a cellulose blank structure.

BACKGROUND

Cellulose fibers are often used as raw material for producing or manufacturing cellulose products. Products formed of cellulose fibers can be used in many different situations where there is a need for having sustainable products. A wide range of cellulose products can be produced from cellulose fibers and a few examples are disposable plates and cups, cutlery, lids, bottle caps, coffee pods, and packaging materials.

One development in the field of producing cellulose products is the forming of cellulose fibers in a dry-forming process, without using traditional wet-forming methods. Instead of forming the cellulose products from a liquid or semi liquid pulp suspension or slurry, an air-formed cellulose blank structure is used. The air-formed cellulose blank structure is inserted into forming molds of a pressing module and during the forming of the cellulose products the cellulose blank structure is subjected to a high forming pressure and a high forming temperature in the forming molds. The pressing module may form part of a product forming unit, and the product forming unit may further comprise other systems, modules, and components, that are arranged in connection to the pressing module in the product forming unit, such as for example feeding modules, buffering modules, and blank dry forming modules.

Another system often used in the product forming unit is an application system for the application of a liquid composition onto the cellulose blank structure. Different compositions may be needed for altering the characteristics of the produced cellulose products, such as for example compositions altering mechanical, hydrophobic, and/or oleophobic properties. The cellulose blank structure is suitably a fluffy and airy structure, where the cellulose fibers forming the structures are arranged relatively loosely in relation to each other. The fluffy cellulose blank structures are used for an efficient forming of the cellulose products, allowing the cellulose fibers to form the cellulose products in an efficient way during the forming process. It is difficult to detect if the liquid composition has been applied to the cellulose blank structure in a proper way, due to the fast absorption of the composition into the fluffy fibrous structure, and because liquid compositions used commonly are transparent or white and problematic to optically distinguish from the cellulose blank structure. If the liquid composition is not applied with correct amounts and in specified areas of the cellulose blank structure, desired properties of the cellulose products may not be achieved and quality issues may arise.

There is thus a need for an improved method for detecting a liquid composition applied onto a cellulose blank structure

2 with a detection system, and an improved detection system for detecting a liquid composition applied onto a cellulose blank structure.

SUMMARY

An object of the present disclosure is to provide a method for detecting a liquid composition applied onto a cellulose blank structure with a detection system, and a detection system, where the previously mentioned problems are avoided. This object is at least partly achieved by the features of the independent claims. The dependent claims contain further developments of the method for detecting a liquid composition.

The disclosure concerns a method for detecting a liquid composition applied onto a cellulose blank structure, with a detection system. The detection system is forming part of a cellulose product forming unit for forming cellulose products from the cellulose blank structure. The detection system comprises a detection unit connected to a control unit. The method comprises the steps: providing the cellulose blank structure and feeding the cellulose blank structure in a feeding direction, where the cellulose blank structure upon feeding is moving through an application area and a detection area, where the application area is arranged upstream the detection area; applying the liquid composition onto the cellulose blank structure in the application area; detecting the applied liquid composition in the detection area with the detection unit, where the detection by the detection unit is forming a detection result; analyzing the detection result by the control unit, where the analysis of the detection result is forming an analysis result; initiating a control action by the control unit upon detection of an analysis result deviating from a pre-determined analysis result.

Advantages with these features are that manufacturing of faulty products can be avoided through the control action. The control action is thus used for avoiding that products with defects due to improper application of the liquid composition is manufactured. Such defective products may for example have reduced ability to withstand liquids or oil based compositions. The defects are detected when the analysis result is deviating from the pre-determined analysis result. The configuration of the fluffy fibrous cellulose blank structures makes it difficult to detect if the liquid composition has been applied to the cellulose blank structure in a proper way, due to for example fast absorption of the liquid composition, and because liquid compositions used commonly are transparent or white and problematic to distinguish from the cellulose blank structure. With the method, it can efficiently be detected if the liquid composition is applied with correct amounts and in specified areas of the cellulose blank structure, due to the detection of the applied liquid composition in the detection area with the detection unit and the comparison between the analysis result and the pre-determined analysis result. The method is efficiently securing that desired properties of the cellulose products are achieved.

In one embodiment, the detection unit comprises an infrared detection sensor. The method further comprises the steps: detecting the applied liquid composition in the detection area with the infrared detection sensor, where the detection result is a temperature image of the detection area; and analyzing the temperature image by the control unit for forming the analysis result. The infrared detection sensor is used for efficiently determining if the liquid composition has been correctly applied onto the cellulose blank structure through the produced temperature image. The temperature image is providing a detection result and identification of temperature value ranges or temperature value fluctuations in the temperature image may be used for determining if the liquid composition has been applied in a correct way.

According to an embodiment, the analysis result comprises temperature values of the detection area and the pre-determined analysis result comprises pre-defined temperature values. The method further comprises the step: initiating the control action by the control unit when the analysis result is a temperature value in any part of the detection area above or below the pre-defined temperature values. According to the method, the temperature values of the temperature image forming the analysis result is compared to the corresponding pre-defined temperature values of the pre-determined analysis result. If the analysis result is deviating from the pre-determined analysis result in any part, the control action is initiated, and the deviation may include threshold values that are specifying how large the deviation should be before the control action is initiated. The deviation of the temperature values of the analysis result may take place in the whole detection area, or in one or more parts of the detection area.

According to an embodiment, the analysis result comprises a mean temperature value of the detection area and the pre-determined analysis result is a pre-defined mean temperature value. The method further comprises the step: initiating the control action by the control unit when the analysis result is a mean temperature value above or below the pre-defined mean temperature value. The use of mean temperature values is one efficient way to determine the deviation in order to initiate the control action. The mean temperature value detected in the analysis result is compared to a pre-determined mean temperature value forming the pre-determined analysis result. The deviation may include a threshold value for the mean temperature value that is specifying how large the deviation should be before the control action is initiated.

In a further embodiment, the method further comprises the step: continuously detecting the applied liquid composition in the detection area by the detection unit. A continuous detection may be used for an efficient detection result through for example the use of a detected video sequence of a moving cellulose blank structure. The produced video sequence may be produced as a continuous sequence for forming the detection result in order to establish the analysis result.

In a further embodiment, the method further comprises the step: intermittently detecting the applied liquid composition in the detection area by the detection unit. An intermittent detection may be used for an efficient detection result through for example the use of a plurality of detected video sequences or still images of a moving cellulose blank structure. The produced video sequences may be produced as a plurality of following video sequences having pre-determined time intervals. Alternatively, an intermittent stream of images is produced for forming the detection result, such as a sequence of still images that is further analyzed by the control unit in order to establish the analysis result.

In a further embodiment, the liquid composition is applied onto the cellulose blank structure in the application area by an application unit. The method further comprises the step: stopping the application of the liquid composition onto the cellulose blank structure by the application unit in the application area as the control action. By stopping the application of the liquid composition as the control action, it is possible to prevent that the liquid composition is applied to the cellulose blank structure in a faulty manner. When the application of the liquid composition has been stopped, further actions can be taken to ensure that the liquid composition can be applied correctly again. An operator of the cellulose product forming unit may for example be notified when the application of the liquid composition has been stopped in order to prevent that defective products are produced, by for example shutting down the cellulose product forming unit. This preventive action may also be automated by the control unit.

According to an embodiment, the method further comprises the step: initiating a cleaning operation of the application unit after stopping the application of the liquid composition onto the cellulose blank structure by the application unit. The cleaning operation is used for eliminating problems in the application unit. Such problems may for example arise if one or more of spray nozzles forming the application unit is not working properly. A malfunctioning spray nozzle may for example be clogged and the cleaning operation is securing that a clogged nozzle is working properly again.

In a further embodiment, the cellulose product forming unit comprises one or more forming molds for forming cellulose products. The method further comprises the steps: stopping a movement of the one or more forming molds as the control action. By stopping the forming molds as the control action, it is possible to prevent that defective products are produced.

In further embodiments, the method further comprises the steps: marking one or more cellulose products and/or the cellulose blank structure as the control action. By marking products and/or parts of the cellulose blank structure that have not been properly applied with the liquid composition as the control action, it is possible to use a detection system for removing marked products or cellulose blank structure. The marking may for example include a color marking operation and products or cellulose blank structure with the color marking may be detected and removed to prevent that defective products are produced. Alternatively, the products and/or the cellulose blank structure may be marked digitally by the control unit. The control unit is storing digitally marked products or sections of the cellulose blank structure in a memory unit in order to remove the digitally marked products or sections at a later operational step where the products or parts of the cellulose blank structure for example are sorted out from the cellulose product forming unit.

In a further embodiment, the amount of liquid composition applied onto the cellulose blank structure in the application area is changed as the control action. By changing the amount of liquid composition, the deviation of the analysis result from the pre-determined analysis result can be corrected. If for example it is detected that the amount of applied liquid composition in an area of the cellulose blank structure is insufficient, the control unit could instruct the application unit to apply a higher amount of liquid composition in that specific area. Alternatively, if it is detected that the amount of applied liquid composition in an area of the cellulose blank structure is too high, the control unit could instruct the application unit to apply a lower amount of liquid composition in that specific area.

In a further embodiment, the liquid composition is applied onto the cellulose blank structure in two or more sub-steps, where in each sub-step a part of the liquid composition is applied onto the cellulose blank structure. As an example, a first row of spray nozzles may be used for spraying a first part of the liquid composition onto the cellulose blank structure and a second row of spray nozzles may be used for spraying a second part of the liquid composition onto the cellulose blank structure. The first part and the second part are together forming the liquid composition applied to the cellulose blank structure.

According to an embodiment, a temperature of each part of the liquid composition is different from the other parts. Thus in the example above, the first part and the second part of the liquid composition may have different temperatures when applied to the cellulose blank structure, and by using different temperatures the control unit could when analyzing the detection result to form the analysis result determine if a temperature deviation in the cellulose blank structure is dependent on a faulty application of either the first part or the second part of the liquid composition.

The disclosure further concerns a detection system for detecting a liquid composition applied onto a cellulose blank structure upon feeding the cellulose blank structure in a feeding direction through an application area and a detection area. The detection system is forming part of a cellulose product forming unit for forming cellulose products from the cellulose blank structure. The detection system comprises a detection unit connected to a control unit, where the detection unit is configured for detecting the applied liquid composition in the detection area arranged downstream an application area in which the liquid composition is applied onto the cellulose blank structure. The detection by the detection unit is forming a detection result. The control unit is configured for analyzing the detection result, and the analysis of the detection result is forming an analysis result. The control unit is configured for initiating a control action upon detection of an analysis result deviating from a pre-determined analysis result.

Advantages with these features are that manufacturing of faulty products can be avoided through the control action. The defects are detected when the analysis result is deviating from the pre-determined analysis result. The configuration of the fluffy fibrous cellulose blank structures makes it difficult to detect if the liquid composition has been applied to the cellulose blank structure in a proper way, due to for example fast absorption of the liquid composition, and because liquid compositions used commonly are transparent or white and problematic to distinguish from the cellulose blank structure. With the system, it can efficiently be detected if the liquid composition is applied with correct amounts and in specified areas of the cellulose blank structure, due to the detection of the applied liquid composition in the detection area with the detection unit and the comparison between the analysis result and the pre-determined analysis result. The system is efficiently securing that desired properties of the cellulose products are achieved.

BRIEF DESCRIPTION OF THE DRAWINGS

The disclosure will be described in detail in the following, with reference to the attached drawings, in which.

DETAILED DESCRIPTION OF THE DRAWINGS

Figure 1A:
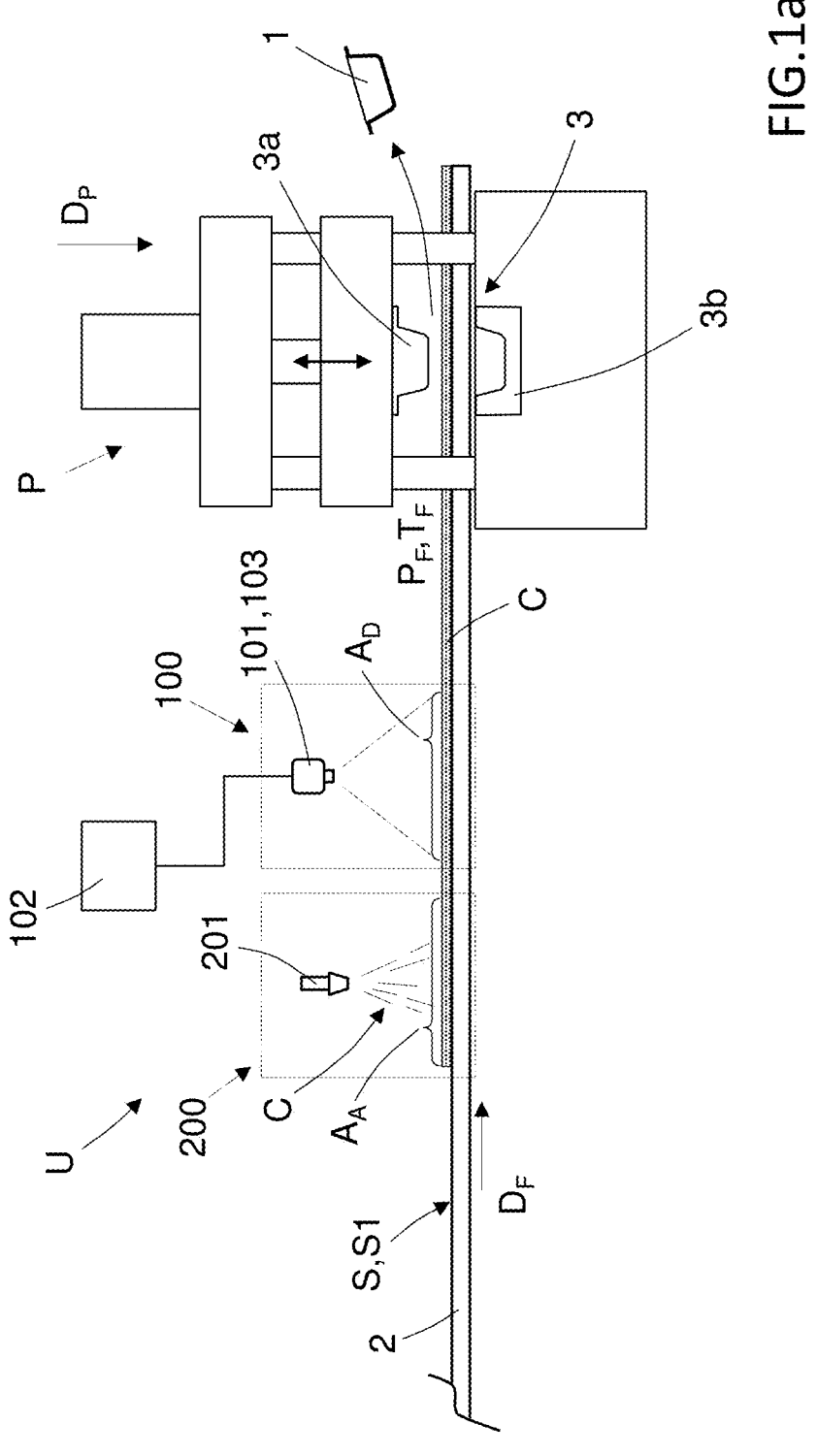
FIG. 1a-b show schematically, in a side view and in a perspective view, a cellulose product forming unit for forming cellulose products from a cellulose blank structure, where the cellulose product forming unit comprises a detection system and an application system.

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure.

Those skilled in the art will appreciate that the steps, services and functions explained herein may be implemented using individual hardware circuitry, using software functioning in conjunction with a programmed microprocessor or general purpose computer, using one or more Application Specific Integrated Circuits (ASICs) and/or using one or more Digital Signal Processors (DSPs). It will also be appreciated that when the present disclosure is described in terms of a method, it may also be embodied in one or more processors and one or more memories coupled to the one or more processors, wherein the one or more memories store one or more programs that perform the steps, services and functions disclosed herein when executed by the one or more processors.

FIGS. 1a-b and 2a-e schematically show a first embodiment of a cellulose product forming unit U for forming cellulose products 1 from a cellulose blank structure 2 in a pressing module P.

To form the non-flat cellulose products 1 from the air-formed cellulose blank structure 2 in the product forming unit U, the cellulose blank structure 2 is first provided from a suitable source. The cellulose blank structure 2 is suitably air-formed from cellulose fibers and arranged on non-illustrated rolls or in stacks. The rolls or stacks may thereafter be arranged in connection to the product forming unit U. As an alternative, the cellulose blank structure 2 may be air-formed from cellulose fibers directly in a blank dry-forming module of the product forming unit U and fed to the pressing module P. The cellulose blank structure 2 is fed the pressing module P with suitable transportation means, such as for example forming wires, vacuum belt feeders, or conveyor belts.

With an air-formed cellulose blank structure 2 is meant an essentially air-formed fibrous web structure produced from cellulose fibers. The cellulose fibers may originate from a suitable cellulose raw material, such as a pulp material. Suitable pulp materials are for example fluff pulp, paper structures, or other cellulose fiber containing structures. With air-forming of the cellulose blank structure 2 is meant the formation of a cellulose blank structure in a dry-forming process in which the cellulose fibers are air-formed to produce the cellulose blank structure 2. When forming the cellulose blank structure 2 in the air-forming process, the cellulose fibers are carried and formed to the fiber blank structure 2 by air as carrying medium. This is different from a normal papermaking process or a traditional wet-forming process, where water is used as carrying medium for the cellulose fibers when forming the paper or fiber structure. In the air-forming process, small amounts of water or other substances may if desired be added to the cellulose fibers in order to change the properties of the cellulose product, but air is still used as carrying medium in the forming process. The cellulose blank structure 2 may, if suitable have a dryness that is mainly corresponding to the ambient humidity in the atmosphere surrounding the air-formed cellulose blank structure 2. As an alternative, the dryness of the cellulose blank structure 2 can be controlled in order to have a suitable dryness level when forming the cellulose products 1.

The air-formed cellulose blank structure 2 may be formed of cellulose fibers in a conventional air-forming process or in a blank dry-forming module. For example, the cellulose blank structure 2 may have a composition where the fibers are of the same origin or alternatively contain a mix of two or more types of cellulose fibers, depending on the desired properties of the cellulose products 1. The cellulose fibers used in the cellulose blank structure 2 are during the forming process of the cellulose products 1 strongly bonded to each other with hydrogen bonds. The cellulose fibers may be mixed with other substances or compounds to a certain amount as will be further described below. With cellulose fibers is meant any type of cellulose fibers, such as natural cellulose fibers or manufactured cellulose fibers. The cellulose blank structure 2 may specifically comprise at least 95% cellulose fibers, or more specifically at least 99% cellulose fibers.

The air-formed cellulose blank structure 2 may have a single-layer or a multi-layer configuration. A cellulose blank structure 2 having a single-layer configuration is referring to a structure that is formed of one layer containing cellulose fibers. A cellulose blank structure 2 having a multi-layer configuration is referring to a structure that is formed of two or more layers comprising cellulose fibers, where the layers may have the same or different compositions or configurations.

The cellulose blank structure 2 may comprise one or more additional cellulose layers comprising cellulose fibers, where an additional cellulose layer may be arranged as a carrying layer for one or more other layers of the cellulose blank structure 2. The one or more additional cellulose layers may act as reinforcement layers having a higher tensile strength than other layers of the cellulose blank structure 2. This is useful when one or more air-formed layers of the cellulose blank structure 2 have compositions with low tensile strength in order to avoid that the cellulose blank structure 2 will break during the forming of the cellulose products 1. The one or more additional cellulose layers with higher tensile strength act in this way as a supporting structure for other layers of the cellulose blank structure 2. The one or more additional cellulose layers may be of a different composition than the rest of the cellulose blank structure, such as for example a tissue layer containing cellulose fibers, an air laid structure comprising cellulose fibers, or other suitable layer structures. It is thus not necessary that the one or more additional cellulose layers are air-formed. Other suitable additional layers may also be used such as for example silicone coated structures or bio-based films.

The cellulose blank structure 2 may further comprise one or more barrier layers giving the cellulose products the ability to hold or withstand liquids, such as for example when the cellulose products 1 are used in contact with beverages, food, and other water-containing substances. The barrier layer may be of a different composition than the rest of the cellulose blank structure 2, such as for example a tissue barrier structure.

The one or more air-formed layers of the cellulose blank structure 2 are fluffy and airy structures, where the cellulose fibers forming the structures are arranged relatively loosely in relation to each other. The fluffy cellulose blank structures 2 are used for an efficient forming of the cellulose products 1, allowing the cellulose fibers to form the cellulose products 1 in an efficient way during the forming process in the pressure module P.

The pressure module P comprises one or more forming molds 3, and the one or more forming molds 3 are configured for forming the cellulose products 1 from the cellulose blank structure 2. The pressing module P may be arranged with only one forming mold 3 in a single-cavity configuration, or alternatively with two or more forming molds in a multi-cavity configuration. A single-cavity configuration pressing module P thus comprises only one forming mold 3 with a first mold part 3a and a cooperating second mold part 3b. A multi-cavity configuration pressing module P comprises two or more forming molds 3, each having cooperating first mold parts 3a and second mold parts 3b.

Figure 1B:
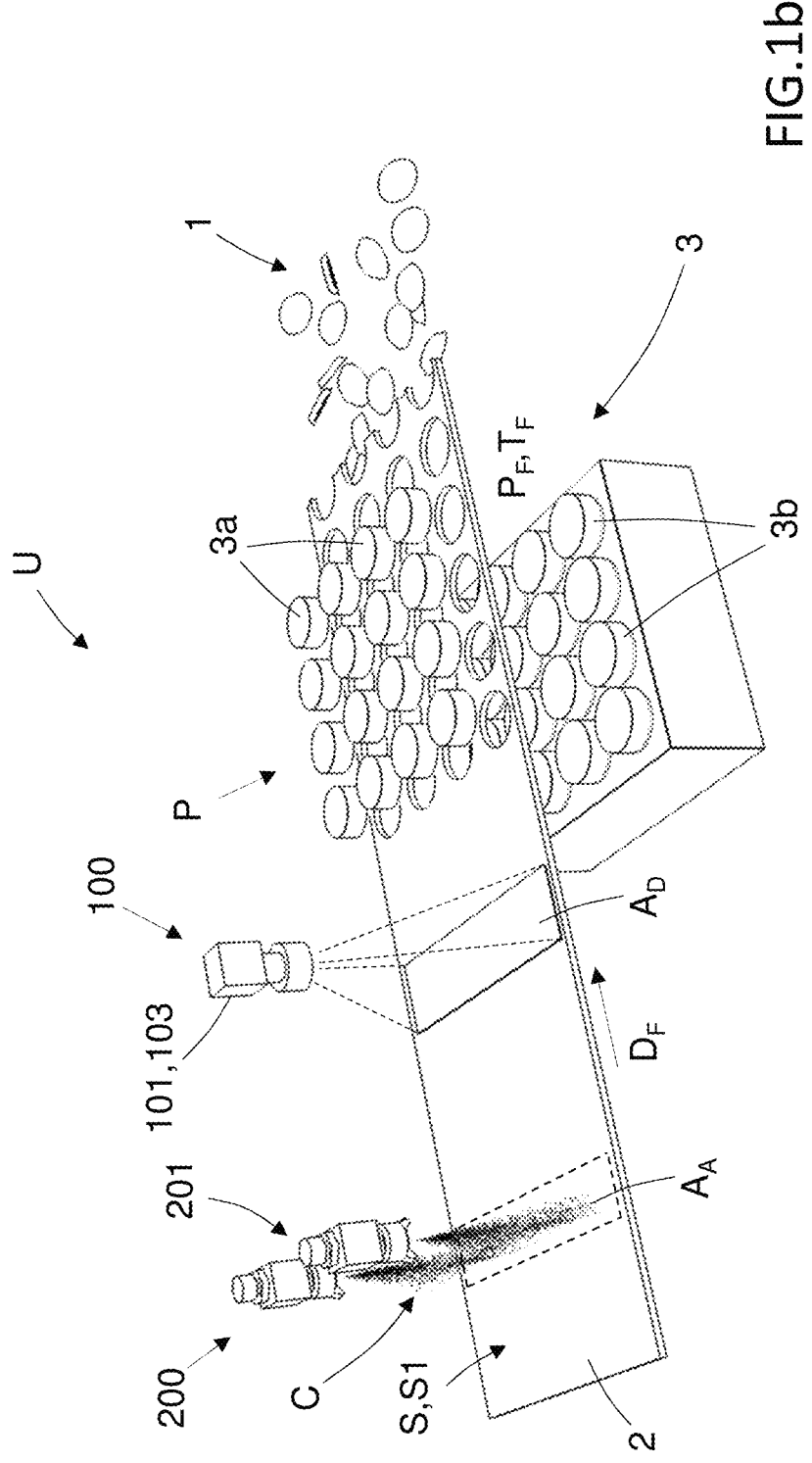

In the embodiment illustrated in FIGS. 1a-b, the pressing module P is arranged as a multi-cavity configuration pressing module P comprising a plurality of forming molds 3 with first mold parts 3a and second mold parts 3b movably arranged in relation to each other, where movements of the mold parts during a product forming operation suitably are synchronized for a simultaneous pressing operation. In the following, the pressing module P will be described in connection to a multi-cavity configuration pressing module, but the disclosure is equally applicable on a single-cavity configuration pressing module.

The pressing module P can for example be constructed so that the first mold parts 3a or the second mold parts 3b are movable and arranged to move towards the other mold part during the forming process, where the other mold part is stationary or non-movably arranged. In the embodiment illustrated in FIGS. 1a-b, the first mold parts 3a are movably arranged and the second mold parts 3b are stationary. In an alternative solution, both the first mold parts 3a and the second mold parts 3b are movably arranged, where the first mold parts 3a and the second mold parts 3b are displaced in directions towards each other during the forming process. The moving mold parts may be displaced with a suitable actuator, such as a hydraulic, pneumatic, or electric actuator. A combination of different actuators may also be used. The relative speed between the first mold part 3a and the second mold part 3b during the forming process is suitably chosen so that the cellulose blank structure 2 is evenly distributed in the one or more forming molds 3 during the forming process.

As indicated in FIG. 1a, the first mold parts 3a are movably arranged in relation to the second mold parts 3b in a pressing direction $D_P$ and the first mold parts 3a are further arranged to be pressed towards the second mold parts 3b during forming of the cellulose products 1 for establishing a forming pressure $P_F$. When forming the cellulose products 1, the cellulose blank structure 2 is arranged between the first mold parts 3a and the second mold parts 3b when the forming molds 3 are in an open state. When the cellulose blank structure 2 has been arranged in the forming molds 3, the first mold parts 3a are moved in relation to the second mold parts 3b during the forming process. When a suitable forming pressure $P_F$ and forming temperature $T_F$ is established in the forming molds 3, the movement of the first mold parts 3$a$ is stopped. The first mold parts 3$a$ are thereafter moved in a direction away from the second mold parts 3$b$ after a certain time period or directly after the first mold parts 3$a$ have been stopped. A suitable control system may be used for controlling the operation of the forming molds 3.

The cellulose products 1 are formed from the cellulose blank structure 2 in the forming molds 3 by heating the cellulose blank structure 2 to a forming temperature $T_F$ in the range of 100-300° C., and pressing the cellulose blank structure 2 with a forming pressure $P_F$ in the range of 1-100 MPa, preferably 4-20 MPa. The first mold parts 3$a$ are arranged for forming the cellulose products 1 through interaction with corresponding second mold parts 3$b$, as exemplified in FIGS. 1$a$-$b$. During forming of the cellulose products 1, the cellulose blank structure 2 is arranged in the one or more forming molds 3, between the first mold parts 3$a$ and the second mold parts 3$b$, and exerted to the forming pressure $P_F$ in the range of 1-100 MPa, preferably in the range of 4-20 MPa, and the forming temperature $T_F$ in the range of 100-300° C. When forming the cellulose products 1, strong hydrogen bonds are formed between the cellulose fibers in the cellulose blank structure 2 arranged between the first mold parts 3$a$ and the second mold parts 3$b$. The temperature and pressure levels are for example measured in the cellulose blank structure 2 during the forming process with suitable sensors arranged in or in connection to the cellulose fibers in the cellulose blank structure 2.

The cellulose blank structure 2 is, as indicated in FIGS. 1$a$-$b$, transported to the forming molds 3 in a feeding direction $D_F$ with a suitable transportation speed. In order to form the cellulose products 1, the cellulose blank structure 2 is arranged between the first mold parts 3$a$ and the second mold parts 3$b$. When forming the cellulose products 1, a force is applied to the first mold parts 3$a$ and/or the second mold parts 3$b$, and the applied force is during the forming process establishing the forming pressure $P_F$ onto the cellulose blank structure 2.

The cellulose blank structure 2 may be arranged into the forming molds 3 in any suitable way, and as an example, the cellulose blank structure 2 may be fed with a suitable feeding device, which is transporting the cellulose blank structure 2 to the forming molds 3 in the feeding direction $D_F$. The feeding device could for example be a conveyor belt, a forming wire unit, an industrial robot, or any other suitable manufacturing equipment. The transportation speed may differ depending on the types of cellulose products 1 produced, and is chosen to match the forming speed in the forming molds 3.

It should be understood that the one or more forming molds 3 may have other designs and constructions compared to the ones described above, such as for example a rotary forming mold construction. The one or more forming molds 3 may also for example be arranged with a cutting device, where the cellulose products 1 are cut into a desired shape in the one or more forming molds 3 during the forming process. When the cellulose products 1 have been cut from the cellulose blank structure 2 in the forming process, a remaining residual cellulose fiber structure is formed. The residual cellulose fiber structure may be recycled and used again when air-forming new cellulose blank structures 2.

A desired property of the cellulose products 1 may be the ability to hold or withstand liquids, such as for example when the cellulose products are used in contact with beverages, food, and other water-containing substances. Compositions or additives used when producing cellulose products in traditional wet-forming processes are for example water based suspensions containing alkyl ketene dimer (AKD) or latex. These compositions or additives may also be used in dry-forming processes, where the air-formed cellulose blank structure 2 is used when forming the cellulose products 1 in the forming molds 3. The compositions or additives are suitably applied to the cellulose blank structure 2 prior to the forming of the cellulose products 1 in the forming molds 3 as a liquid composition C. The liquid compositions C may be water based and comprise any suitable additives or compositions.

The cellulose product forming unit U further comprises a detection system 100 and an application system 200 as shown in FIGS. 1$a$-$b$. The detection system 100 is used for detecting the liquid composition C applied onto the cellulose blank structure 2. The detection system 100 comprises a detection unit 101 connected to a control unit 102. The application system 200 is applying the liquid composition C onto the cellulose blank structure 2. The application system 200 comprises an application unit 201 that is applying an amount of the liquid composition C onto a surface S of the cellulose blank structure 2. The detection system 100 and the application system 200 are forming part of the product forming unit U and may suitably be arranged as modules integrated in the product forming unit U.

As illustrated in FIGS. 1$a$-$b$, the liquid composition C is applied to the surface S of the cellulose blank structure 2 by the application unit 201 of the application system 200. As understood from FIGS. 1$a$-$b$, the liquid composition C is applied to the cellulose blank structure 2 in an application area $A_A$. The application area $A_A$ is defining an area of the product forming unit U through which the cellulose blank structure 2 is fed in the feeding direction $D_F$. The liquid composition C is thus applied onto the cellulose blank structure 2 in the application area $A_A$ upon transportation of the cellulose blank structure 2 in the feeding direction $D_F$, and the application area $A_A$ may have any suitable extension in the feeding direction $D_F$ and in a direction perpendicular to the feeding direction $D_F$. In the illustrated embodiment, the application area $A_A$ has a rectangular-shaped configuration but it should be understood that the application area $A_A$ could have any suitable shape or size. The application unit 201 may for example be arranged with a set of spray nozzles for applying the liquid composition C onto the surface S of the cellulose blank structure 2 in the application area $A_A$. In the embodiment illustrated in FIGS. 1$a$-$b$, the liquid composition is applied from above the cellulose blank structure 2 onto a first surface S1 of the cellulose blank structure 2 with two spray nozzles forming the application unit 201. However, any suitable number of spray nozzles may be used. The spray nozzles may be of any suitable construction for distributing the liquid composition C under hydraulic or pneumatic pressure. The arrangement of spray nozzles may differ from the ones described and illustrated, depending on the configuration, shape, and size of the cellulose blank structure 2. Pulse width modulation with feedback control may suitably be used for controlling the amount of liquid composition C applied onto the cellulose blank structure 2 with the spray nozzles.

The spray nozzles of the application unit 201 in the different embodiments may spray the liquid composition C continuously or intermittently onto the cellulose blank structure 2. The liquid composition C may also be applied with the same or different amounts over the whole cellulose blank structure 2 or only on parts or zones of the cellulose blank structure 2. The spray nozzles may suitably be arranged in a non-illustrated spray booth or similar structure, preventing that the liquid composition C when sprayed are spread into the surrounding environment.

As described above, the cellulose product forming unit U further comprises the detection system 100, as shown in FIGS. 1*a-b*. The detection system 100 is used for detecting that the liquid composition C is correctly applied onto the cellulose blank structure 2, and the detection system 100 comprises the detection unit 101 connected to the control unit 102.

As described above, the cellulose blank structure 2 is a fluffy and airy structure, where the cellulose fibers forming the cellulose blank structure 2 are arranged relatively loosely in relation to each other. With this configuration of the cellulose blank structure 2, it may be difficult to detect if the liquid composition C has been applied to the right area of the cellulose blank structure 2 with the right amounts of liquid composition. Therefore, the detection unit 101 is arranged in connection to a detection area $A_D$ of the product forming unit U, and the detection unit 101 is used for detecting if the liquid composition C has been applied correctly.

When feeding the cellulose blank structure 2 in the feeding direction $D_F$, the cellulose blank structure 2 is moving through the application area $A_A$ and the detection area $A_D$. As understood from for example FIGS. 1*a-b*, the application area $A_A$ is arranged upstream the detection area $A_D$.

With the method, the liquid composition C is applied onto the cellulose blank structure 2 in the application area $A_A$, and thereafter the applied liquid composition C is detected in the detection area $A_D$ with the detection unit 101. The detection by the detection unit 101 is forming a detection result $R_D$. The detection result $R_D$ is analyzed by the control unit 102, and the analysis of the detection result $R_D$ is forming an analysis result $R_A$. Upon detection of an analysis result $R_A$ deviating from a pre-determined analysis result $R_{APD}$, a control action CA is initiated by the control unit 102. The detection of the deviation of the analysis results is achieved by comparing the analysis result $R_A$ with the pre-determined analysis result $R_{APD}$. The control action CA is preventing that cellulose products 1 with non-desired properties are produced, as will be further described below.

The detection unit 101 may be arranged as a thermal imaging unit comprising infrared thermography technology. The detection unit 101 may thus comprise an infrared detection sensor 103, and the infrared detection sensor 103 is suitably a thermographic camera or similar sensor for thermal imaging or thermal video detection. The applied liquid composition C is detected in the detection area $A_D$ with the infrared detection sensor 103, where the detection result $R_D$ is a temperature image I of the detection area $A_D$ captured by the infrared detection sensor 103. The infrared detection sensor 103 is producing temperature images I of a section of the cellulose blank structure 2 positioned in the detection area $A_D$, when the cellulose blank structure 2 is fed in the feeding direction $D_F$. The temperature image I is analyzed by the control unit 102 for forming the analysis result $R_A$.

The infrared detection sensor 103 may continuously monitor the detection area $A_D$, where a continuous stream of images is produced for forming the detection result $R_D$, such as a video sequence that is further analyzed by the control unit 102 in order to establish the analysis result $R_A$. The produced video sequence may be produced as a continuous sequence or alternatively as a plurality of following video sequences having pre-determined time intervals. In this embodiment, the applied liquid composition C is thus continuously detected in the detection area $A_D$ by the detection unit 101.

The infrared detection sensor 103 may alternatively intermittently monitor the detection area $A_D$, where an intermittent stream of images is produced for forming the detection result $R_D$, such as video sequences or a sequence of still images that is further analyzed by the control unit 102 in order to establish the analysis result $R_A$. The produced sequence may thus comprise a plurality of still images that are forming the detection result, where each image is analyzed to form the analysis result $R_A$. The still images are suitably captured by the infrared detection sensor 103 with pre-determined time intervals. In this embodiment, the applied liquid composition C is thus intermittently detected in the detection area $A_D$ by the detection unit 101.

The pre-determined analysis result $R_{APD}$ can be seen as a reference temperature image $I_{REF}$ formed as a reference still image or video sequence of the detection area $A_D$ for the specific liquid composition C and cellulose blank structure 2, where the reference temperature image $I_{REF}$ is showing a desired temperature state of the cellulose blank structure 2 with the applied liquid composition C. The reference temperature image $I_{REF}$ may comprise one or more desired zones with pre-determined temperature ranges of the cellulose blank structure 2. If for example the whole area of the cellulose blank structure is applied with the liquid composition C, the reference temperature image $I_{REF}$ may only comprise one temperature range zone. If for example only a part of the whole area of the cellulose blank structure is applied with the liquid composition C, the reference temperature image $I_{REF}$ may comprise two or more temperature range zones.

In the following, the detection result $R_D$ and the analysis result $R_A$ will be described in connection to temperature images I captured as still images by the infrared detection sensor 103 and analyzed by the control unit 102. However, the disclosure is equally applicable on a video sequence or a plurality of video sequences as the detection result $R_D$. The control unit 102 is configured for analyzing still images and/or video sequences, and is arranged with software suitable for image and/or video analysis.

When the liquid composition C has been applied onto the cellulose blank structure 2, the temperature of the applied liquid composition C in the cellulose blank structure 2 is detected with the infrared detection sensor 103. If the liquid composition C is applied onto the cellulose blank structure 2 in a specific pre-determined pattern, a specific temperature pattern is established in the cellulose blank structure 2, for example through cooling effects from evaporation of the applied liquid composition C. The infrared detection sensor 103 is thus used for detecting if the liquid composition C applied onto the cellulose blank structure 2 is following the specific temperature pattern or not, and thus if the evaporation of the applied liquid composition C is occurring in a desired way. The applied liquid composition C is changing the temperature of the cellulose blank structure 2 due to for example absorption and evaporation effects of the liquid composition C when applied to and at least partly absorbed in the cellulose fibers of the cellulose blank structure 2. The control unit 102 is calibrated for a specific application of a specific liquid composition C in a specific cellulose blank structure 2, and these specific parameters are forming the pre-determined analysis result $R_{APD}$. The control unit 102 is programmed to determine if the produced temperature images I forming the analysis result $R_A$ from the detection by the infrared detection sensor 103 are corresponding to the reference temperature image $I_{REF}$ of the pre-determined analysis result $R_{APD}$, or if the produced temperature images I forming the analysis result $R_A$ from the detection by the infrared detection sensor 103 are deviating from the reference temperature image $I_{REF}$ of the pre-determined analysis result $R_{APD}$.

The analysis result $R_A$ and the pre-determined analysis result $R_{APD}$, are affected by conditions such as the temperature of the applied liquid composition C and the temperature of the cellulose blank structure 2. Another condition is the amount of liquid composition C applied to the cellulose blank structure 2, and a higher amount results in a higher evaporation rate and a higher cooling effect. Other conditions affecting the results are the thickness and composition of the cellulose blank structure 2, which are impacting the absorption rate and the evaporation rate of the applied liquid composition C. The control unit 102 may therefore be programmed to consider such conditions when establishing the analysis result $R_A$ and the pre-determined analysis result $R_{APD}$.

The control unit 102 may further be programmed with image analysis software that also considers various other conditions when determining if the produced temperature images I forming the analysis result $R_A$ from the detection by the infrared detection sensor 103 are corresponding to the reference temperature image $I_{REF}$ of the pre-determined analysis result $R_{APD}$.

Such conditions could for example be environmental conditions, as for example temperature variations or humidity variations that are influencing the evaporation of the applied liquid composition C, and thus the analysis result $R_A$. Other conditions may be time based, where the time from spraying the liquid composition C onto the cellulose blank structure 2 to the detection by the infrared detection sensor 103 may be influencing the analysis result $R_A$. Further, minor variations or fluctuations over time may be considered, since these variations or fluctuations may indicate for example a malfunctioning spray nozzle. The control unit 102 may therefore be programmed with specific algorithms and mathematical functions that are taking these conditions into consideration when comparing the analysis result $R_A$ with the pre-determined analysis result $R_{APD}$.

The liquid composition C applied onto the cellulose blank structure 2 in the application area $A_A$ is detected with the infrared detection sensor 103 in the detection area $A_D$, and the detection result $R_D$ is formed as a temperature image I of the detection area $A_D$. When analyzing the detection result $R_D$ in the form of the temperature image I by the control unit 102, the analysis result $R_A$ is established, as will be further described below.

The analysis result $R_A$ comprises temperature values T of the detection area $A_D$ and the pre-determined analysis result $R_{APD}$ comprises one or more pre-defined temperature values $T_{PD}$ of the detection area $A_D$. It should be understood that the temperature values T and the pre-defined temperature values $T_{PD}$ may suitably be arranged as one or more temperature ranges, and that the pre-defined temperature values $T_{PD}$ may differ between parts or sub-areas of the reference temperature image $I_{REF}$ forming the pre-determined analysis result $R_{APD}$. If the analysis result $R_A$ comprises temperature values that are the same or essentially the same as the pre-defined temperature values $T_{PD}$ of the pre-determined analysis result, it can be determined by the control unit 102 that the liquid composition C is correctly applied onto the cellulose blank structure 2. If the analysis result $R_A$ comprises temperature values T that are not the same or essentially the same as the pre-defined temperature values $T_{PD}$ of the pre-determined analysis result, it can be determined by the control unit 102 that the liquid composition C is non-correctly applied onto the cellulose blank structure 2. Thus, for a deviating analysis result $R_A$, the control unit 102 is determining that there are problems with the application of the liquid composition C onto the cellulose blank structure 2. Such problems may for example arise if one or more of the spray nozzles forming the application unit 201 is not working properly. A malfunctioning spray nozzle may for example be clogged or the supply of the liquid composition to the spray nozzle may be interrupted. In other cases, one or more of the spray nozzles may apply a too high amount of liquid composition C. The deviation of the temperature values T of the analysis result $R_A$ may take place in the whole detection area $A_D$, or in one or more parts of the detection area $A_D$.

In the embodiment schematically illustrated in FIGS. 1a-b and 2a-e, the cellulose blank structure 2 with the applied liquid composition C is fed through the detection area $A_D$ in the feeding direction $D_F$. The temperature image I of the detection result $R_D$ comprises detected temperatures of the cellulose blank structure in the detection area $A_D$, and the detected temperatures are when establishing the analysis result $R_A$ transformed into a temperature image I comprising temperature values T of the detection area $A_D$. The temperature values T are suitably formed as one or more temperature zones, where each temperature zone has a specific temperature range. The specific temperature ranges may be based on pre-determined input values and used by the control unit 102 when forming the analysis result $R_A$. Thus, the analysis result $R_A$ is in this way formed as a temperature image I comprising one or more temperature zones.

The pre-determined analysis result $R_{APD}$ comprises one or more pre-defined temperature values $T_{PD}$ of the detection area $A_D$, and the pre-defined temperature values $T_{PD}$ are suitably formed as one or more temperature zones, where each temperature zone has a specific temperature range. Thus, the pre-determined analysis result $R_{APD}$ is in this way formed as a reference temperature image $I_{REF}$ comprising one or more temperature zones.

Figure 2A:
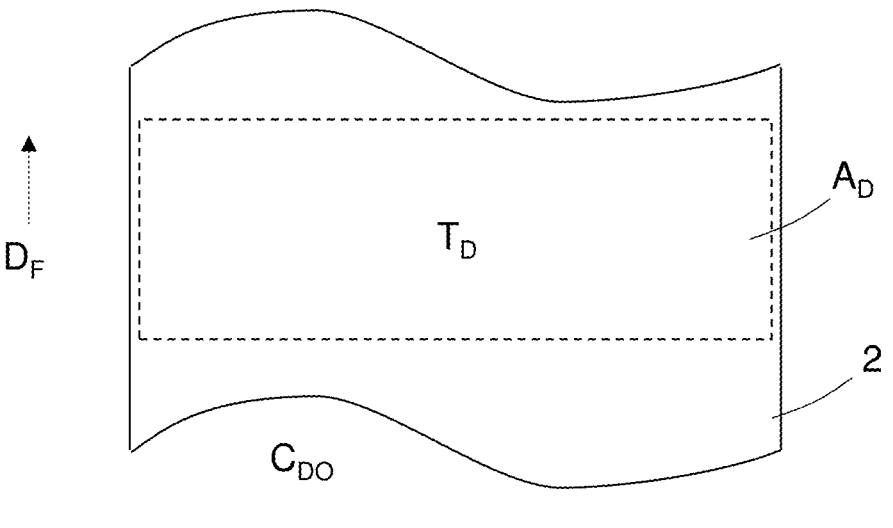
FIG. 2a-e show schematically, in views from above, a detection area of the product forming unit, a reference temperature image, and temperature images of the detection area.
Figure 2B:
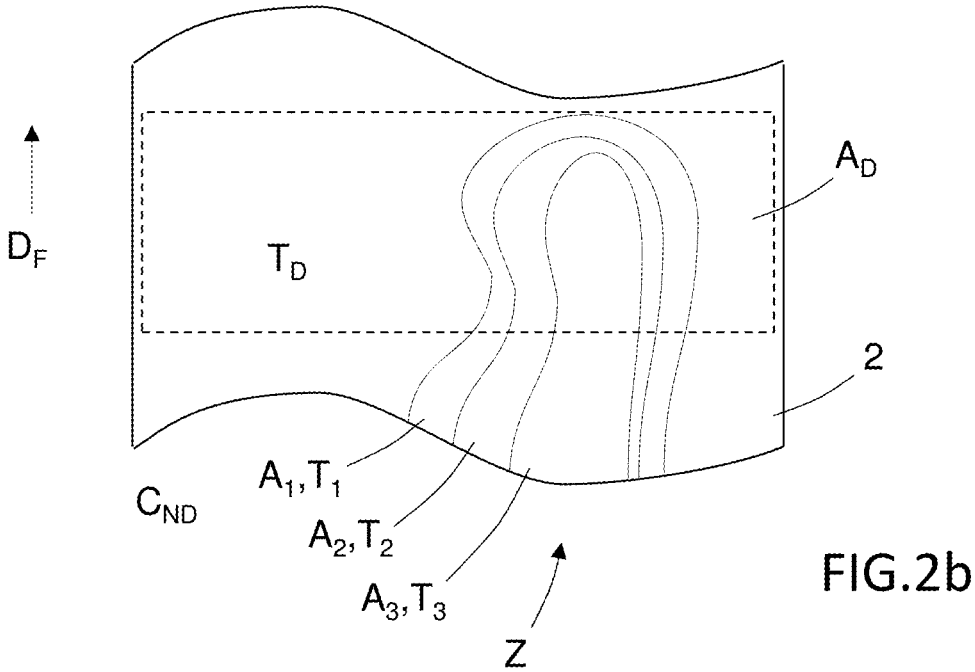
Figure 2C:
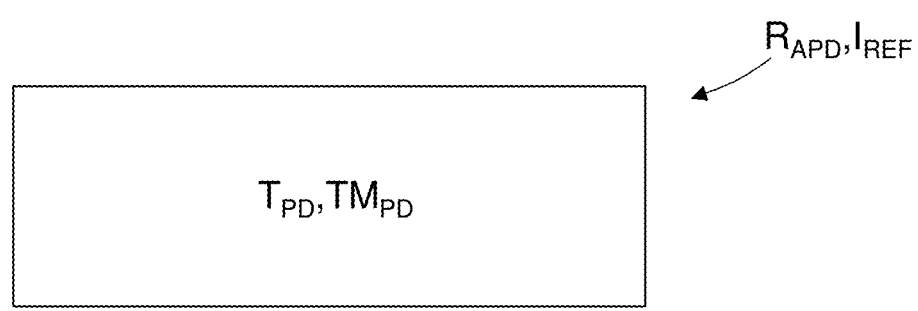
Figure 2D:
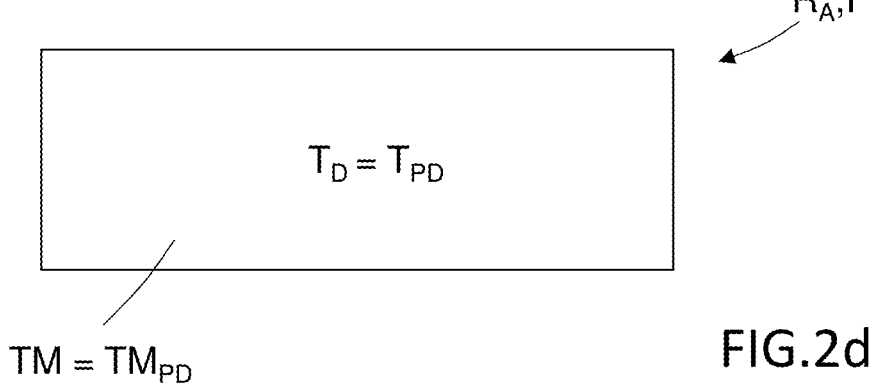
Figure 2E:
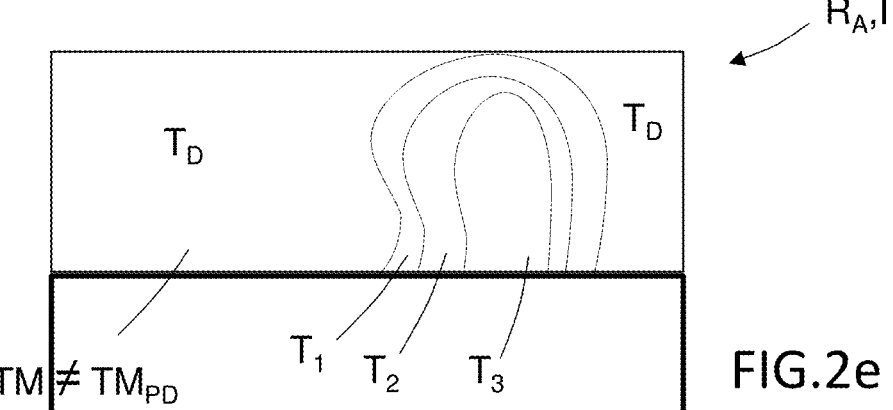

In FIG. 2a, the detection area $A_D$ of the cellulose product forming unit U in the embodiment shown in FIGS. 1a-b is schematically illustrated in a desired operating condition $C_{DO}$. In this embodiment, the liquid composition C is evenly distributed onto the cellulose blank structure 2 in the application area $A_A$ in the desired operating condition $C_{DO}$, which is resulting in an even temperature distribution. In FIG. 2a, a desired temperature value $T_D$ of the cellulose blank structure 2 in the desired operating condition $C_{DO}$ is schematically illustrated, and in this embodiment it is assumed that the temperature of the cellulose blank structure 2 with the applied liquid composition C in the detection area $A_D$ has the desired temperature value $T_D$ or essentially the desired temperature value $T_D$. It should be understood that the desired temperature value $T_D$ of the detection area $A_D$ in the desired operating condition $C_{DO}$ could include a temperature range with minor temperature variations. Based on this desired operating condition $C_{DO}$, the pre-determined analysis result $R_{APD}$ can be determined, and arranged as the reference temperature image $I_{REF}$ with the pre-defined temperature value $T_{PD}$. In this embodiment, the reference temperature image $I_{REF}$ of the pre-determined analysis result $R_{APD}$ comprises one pre-defined temperature value $T_{PD}$, where the pre-defined temperature value $T_{PD}$ may be a temperature range with minor temperature variations. In FIG. 2c, the reference temperature image $I_{REF}$ with the pre-defined temperature value $T_{PD}$ of the pre-determined analysis result $R_{APD}$ is schematically illustrated. In FIG. 2$d$, the temperature image I with the desired temperature value $T_D$ of the analysis result $R_A$ in the desired operating condition $C_{DO}$ is schematically illustrated. In this case, the reference temperature image $I_{REF}$ with the pre-defined temperature value $T_{PD}$, as shown in FIG. 2$c$, is corresponding to the temperature image I with the desired temperature value $T_D$ in the desired operating condition $C_{DO}$, as shown in FIG. 2$d$. Thus, in the desired operating conditions $C_{DO}$, the desired temperature value $T_D$ and the pre-defined temperature value $T_{PD}$ are the same or essentially the same, and the analysis result $R_A$ in the form of the temperature image I of the detection area $A_D$ based on the detection result $R_D$ is corresponding to the reference temperature image $I_{REF}$. In the desired operating condition $C_{DO}$, the analysis result $R_A$ is not deviating from the pre-determined analysis result $R_{APD}$, and no control action CA is therefore initiated.

In FIG. 2$b$, the detection area $A_D$ of the cellulose product forming unit U in the embodiment shown in FIGS. 1$a$-$b$ is schematically illustrated in a non-desired operating condition $C_{ND}$. In the non-desired operating condition $C_{ND}$, the liquid composition C is unevenly distributed onto the cellulose blank structure 2 in the application area $A_A$ due to for example a malfunctioning spray nozzle or interruption in the supply of the liquid composition C to a spray nozzle, which is resulting in an uneven temperature distribution. In FIG. 2$b$, a temperature zone Z of the cellulose blank structure 2 with deviating temperatures is schematically illustrated. As schematically shown in FIG. 2$b$, the temperature zone Z comprises a first area A, with a first deviating temperature or temperature range $T_1$, a second area $A_2$ with a second deviating temperature or temperature range $T_2$, and a third area $A_3$ with a third deviating temperature or temperature range $T_3$. The part of the cellulose blank structure 2 outside the temperature zone Z is having the desired temperature value $T_D$ as indicated in FIG. 2$b$. Thus, in this embodiment it is assumed that the temperature of the cellulose blank structure 2 with the applied liquid composition C in the detection area $A_D$ outside the temperature zone Z has the desired temperature value $T_D$ or essentially the desired temperature value $T_D$, and that the temperature of the cellulose blank structure 2 with the applied liquid composition C in the temperature zone Z has temperature values deviating from the desired temperature value $T_D$. The temperature values in the temperature zone Z may thus be higher and/or lower than the desired temperature value $T_D$. In the same way as in the embodiment described above, the reference temperature image $I_{REF}$ of the pre-determined analysis result $R_{APD}$ comprises one pre-defined temperature value $T_{PD}$, where the pre-defined temperature value $T_{PD}$ may be a temperature range with minor temperature variations. In FIG. 2$c$, the reference temperature image $I_{REF}$ with the pre-defined temperature value $T_{PD}$ of the pre-determined analysis result $R_{APD}$ is schematically illustrated. In FIG. 2$e$, the temperature image I with the temperature values of the analysis result $R_A$ in the non-desired operating condition $C_{ND}$ is schematically illustrated. As schematically shown in FIG. 2$e$, a major part of the temperature image I has the desired temperature value $T_D$, and in this part it is assumed that the application of the liquid composition C is correct. Due to the deviating temperature values in the temperature zone Z, it is assumed that the application of the liquid composition C is not correct. As schematically shown in FIG. 2$e$, the temperature image I comprises a deviating first temperature or temperature range $T_1$, a deviating second temperature or temperature range $T_2$, and a deviating third temperature or temperature range $T_3$. The deviating temperatures or temperature ranges are higher and/or lower than the desired temperature value $P_D$. In this case, the reference temperature image $I_{REF}$ with the pre-defined temperature value $T_{PD}$, as shown in FIG. 2$c$, is deviating from the temperature image I in the non-desired operating condition $C_{ND}$, as shown in FIG. 2$e$. Thus, in the non-desired operating conditions $C_{ND}$, some of the temperature values of the analysis result $R_A$ and the pre-defined temperature value $T_{PD}$ of the pre-determined analysis result $R_{APD}$ are not the same or essentially the same, and the analysis result $R_A$ in the form of the temperature image I of the detection area $A_D$ based on the detection result $R_D$ is not corresponding to the reference temperature image $I_{REF}$. In the non-desired operating condition $C_{ND}$, the analysis result $R_A$ is deviating from the pre-determined analysis result $R_{APD}$, and the control action CA is therefore initiated.

The control action CA may be used for avoiding that cellulose products 1 with defects due to improper application of the liquid composition C is manufactured. The defects are detected when the analysis result $R_A$ is deviating from the pre-determined analysis result $R_{APD}$, as described above.

As described above, the analysis result $R_A$ may comprise temperature values T of the detection area $A_D$ and the pre-determined analysis result $R_{APD}$ is configured as the pre-defined temperature value $T_{PD}$. The control action CA may be initiated by the control unit 102 when the analysis result $R_A$ is a temperature value T in any part of the detection area $A_D$ above or below the pre-defined temperature value $T_{PD}$, such as for example in the case illustrated in FIG. 2$e$. The temperature values of the temperature image I forming the analysis result is compared to the pre-defined temperature values $T_{PD}$ of the pre-determined analysis result. If the analysis result $R_A$ is deviating from the pre-determined analysis result in any part, the control action CA is initiated. The deviation may include threshold values that are specifying how large the deviation should be before the control action is initiated. The deviation of the temperature values of the analysis result may take place in the whole detection area $A_D$, or in one or more parts of the detection area $A_D$.

Alternatively, the analysis result $R_A$ may instead comprise a mean temperature value TM of the detection area $A_D$ and the pre-determined analysis result $R_{APD}$ is configured as a pre-defined mean temperature value $TM_{PD}$. The control action CA may be initiated by the control unit 102 when the analysis result $R_A$ is a mean temperature value TM above or below the pre-defined mean temperature value $TM_{PD}$. The use of mean temperature values is an alternative suitable way to determine the deviation in order to initiate the control action. The mean temperature value detected in the analysis result is compared to a pre-determined mean temperature value forming the pre-determined analysis result. The deviation may include a threshold value for the mean temperature value that is specifying how large the deviation should be before the control action is initiated. In FIG. 2$c$, the pre-defined mean temperature value $TM_{PD}$ is determined as the mean temperature value of the reference temperature image $I_{REF}$. The analysis result $R_A$ in FIG. 2$d$ is having a mean temperature value TM that is the same as the pre-defined mean temperature value $TM_{PD}$, and therefore no control action CA is initiated. The analysis result $R_A$ in FIG. 2$e$ is having a mean temperature value TM that is different from the pre-defined mean temperature value $TM_{PD}$, and therefore a control action CA is initiated.

It should be understood that for all embodiments, the reference temperature image $I_{REF}$ could instead comprise two or more temperature values for different parts of the detection area $A_D$.

The control action may be arranged in different ways. In one embodiment, the control action CA includes a stopping of the application of the liquid composition C onto the cellulose blank structure 2 by the application unit 201 in the application area $A_A$. By stopping the application of the liquid composition as the control action CA, it is possible to prevent that defective products are produced. A cleaning operation $O_C$ of the application unit 201 could be initiated after stopping the application of the liquid composition C onto the cellulose blank structure 2 by the application unit 201. The cleaning operation $O_C$ is used for eliminating problems in the application unit 201. Such problems may for example arise if one or more of spray nozzles forming the application unit 201 is not working properly. A malfunctioning spray nozzle may for example be clogged and the cleaning operation is securing that a clogged nozzle is working properly again. In the cleaning operation, the spray nozzles may be flushed internally and/or sprayed externally with water or other suitable cleaning liquids or fluids to remove substances that are clogging the spray nozzles or disturbing the nozzle spray pattern. The cleaning operation may include high pressure flushing or spraying for an efficient removal of substances.

In one embodiment, the control action CA includes a stopping of a movement of the one or more forming molds 3. By stopping the forming molds as the control action, it is possible to prevent that defective products are produced.

In one embodiment, the control action CA includes a marking of one or more cellulose products 1 and/or the cellulose blank structure 2. By marking cellulose products 1 and/or parts of the cellulose blank structure 2 that have not been properly applied with the liquid composition C as the control action CA, it is possible to use a suitable detection system for removing marked cellulose products 1 or marked sections of the cellulose blank structure 2. The marking may for example be a color marking operation and cellulose products 1 or the cellulose blank structure 2 with the color marking may be detected and removed to prevent that defective products are produced or further handled. The color marking operation may for example be accomplished with a suitable spray nozzle unit that is color marking the one or more cellulose products or one or more sections of the cellulose blank structure 2 with non-properly applied liquid composition C. Alternatively, the one or more cellulose products 1 or the one or more sections of the cellulose blank structure 2 with non-properly applied liquid composition C, may be marked digitally by the control unit. The control unit is storing the digitally marked products or sections in a memory unit in order to sort out the digitally marked products or sections at a later operational step where the marked products or sections for example are removed from the cellulose product forming unit U.

In one embodiment, the amount of liquid composition C applied onto the cellulose blank structure 2 in the application area $A_A$ is changed as the control action CA. By changing the amount of liquid composition, the deviation of the analysis result $R_A$ from the pre-determined analysis result $R_{APD}$ can be corrected. If it is detected that the amount of applied liquid composition C in an area of the cellulose blank structure 2 is insufficient, the control unit 102 could instruct the application unit 201 to apply a higher amount of liquid composition C in that specific area. Alternatively, if it is detected that the amount of applied liquid composition C in an area of the cellulose blank structure 2 is too high, the control unit 102 could instruct the application unit 201 to apply a lower amount of liquid composition C in that specific area. Changing an amount of the liquid composition C also includes changing a concentration or a viscosity of the liquid composition C.

In an alternative embodiment, a UV detecting sensor could be used as the detection unit 101 instead of using the infrared detection sensor described above. The UV detection sensor is used for detecting ultraviolet light. With this configuration of the detection unit, a UV reflecting pigment composition is added to the liquid composition C, and the UV detection sensor is detecting the amount of particles applied onto the cellulose blank structure. The detection result $R_D$ may be transformed into an image I as the analysis result $R_A$ that is processed in a similar way as the temperature image described above and compared to a reference UV image $I_{REF}$ as the pre-determined analysis result $R_{APD}$.

An alternative embodiment of the product forming unit U is schematically illustrated in FIGS. 3a-b and 4a-e. In this alternative embodiment, the detection system 100 and application system 200 are having different configurations compared to the product forming unit U shown in FIGS. 1a-b. The pressing module P may have the same configuration as the pressing module described above in connection to FIGS. 1a-b.

Figure 3A:
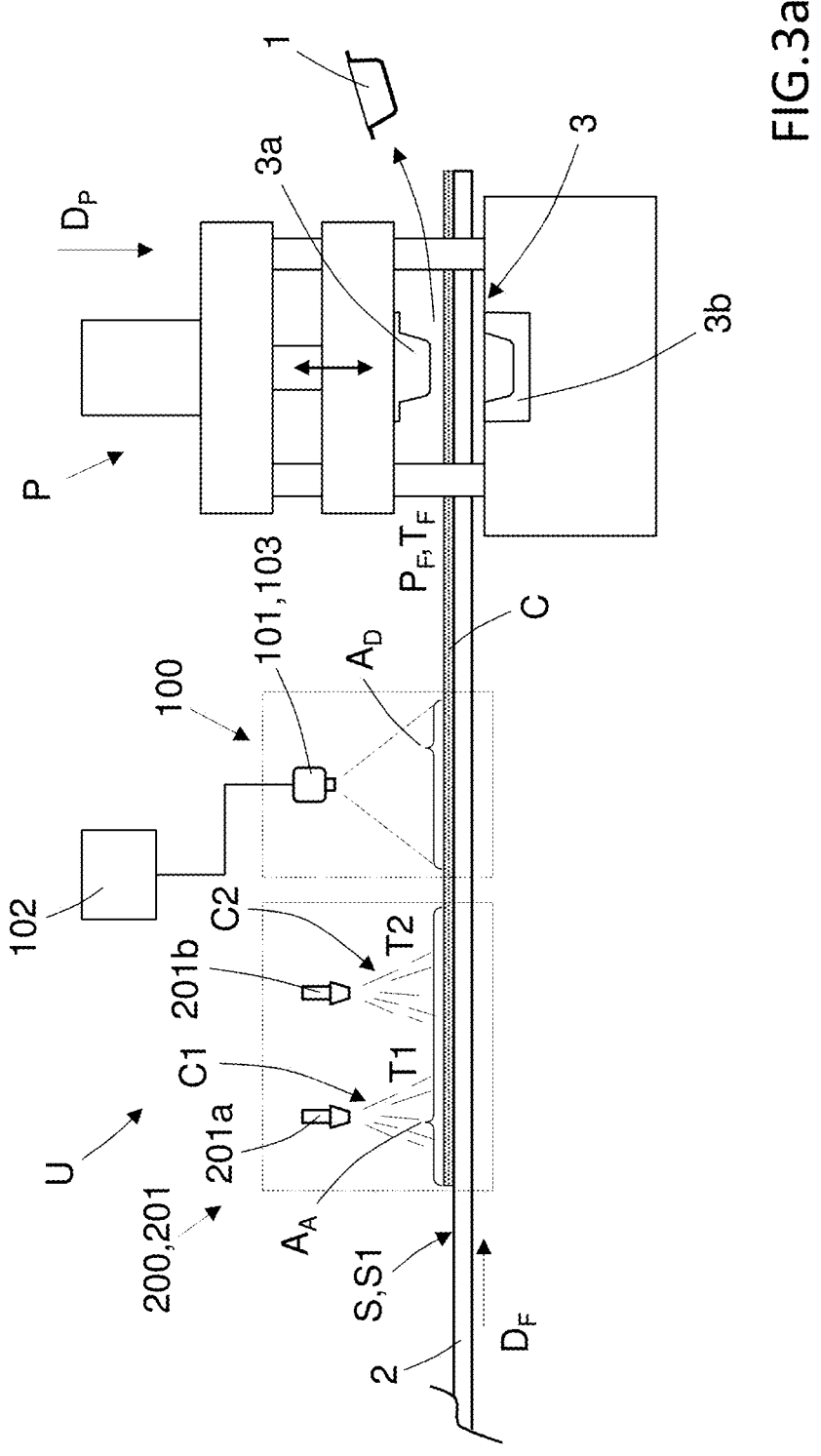
FIG. 3a-b show schematically, in a side view and in a perspective view, an alternative embodiment of a cellulose product forming unit, where the cellulose product forming unit comprises a detection system and an application system.
Figure 3B:
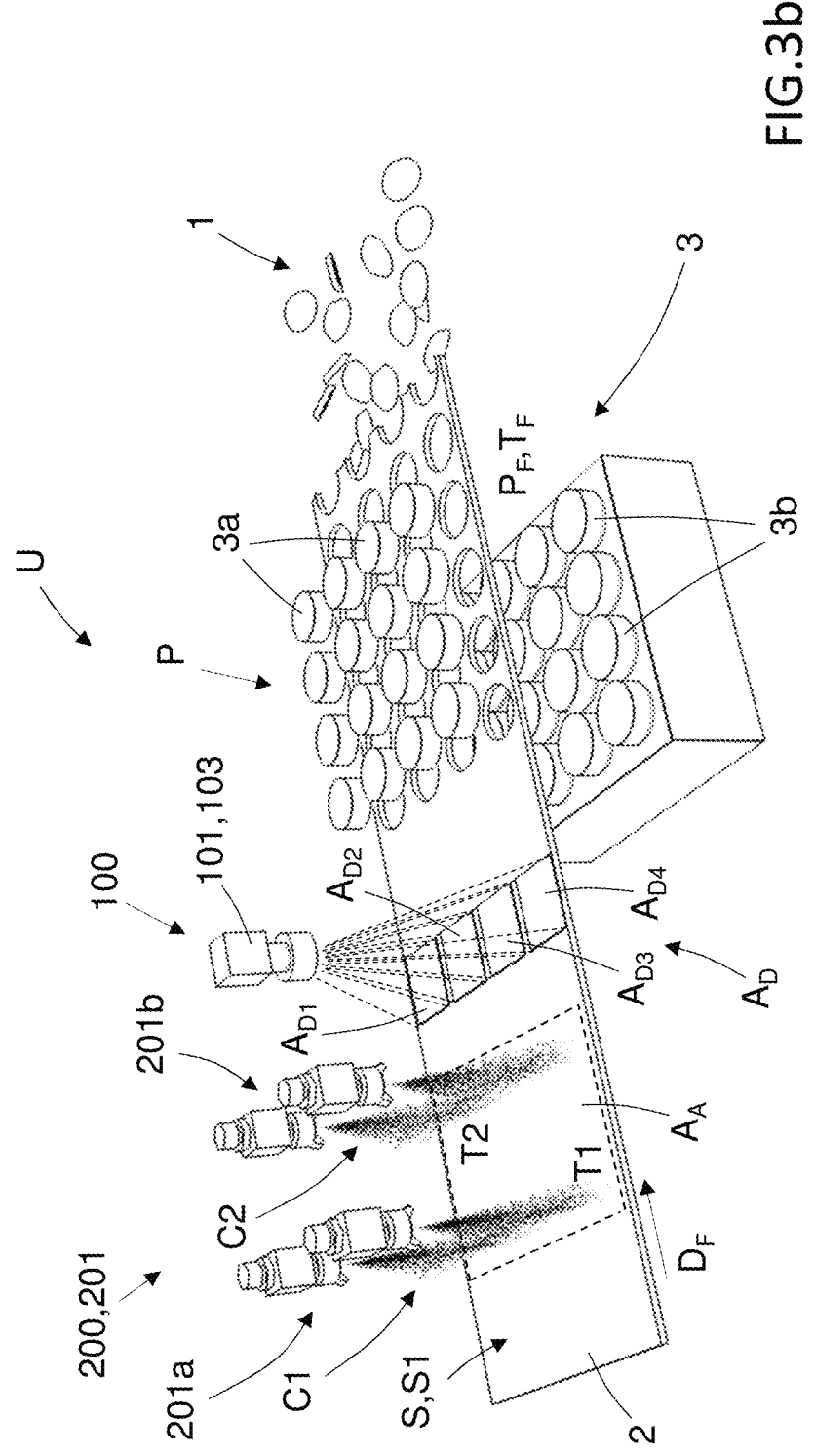

As illustrated in FIGS. 3a-b, the liquid composition C is applied to a surface S of the cellulose blank structure 2 by the application unit 201 of the application system 200. As understood from FIGS. 3a-b, the liquid composition C is applied to the cellulose blank structure 2 in an application area $A_A$. The application area $A_A$ is defining an area of the product forming unit U through which the cellulose blank structure 2 is fed in the feeding direction $D_F$. The liquid composition C is thus applied onto the cellulose blank structure 2 in the application area $A_A$ upon transportation of the cellulose blank structure 2 in the feeding direction $D_F$, and the application area $A_A$ may have any suitable extension in the feeding direction $D_F$ and in a direction perpendicular to the feeding direction $D_F$. In the illustrated embodiment, the application area $A_A$ has a rectangular-shaped configuration, but it should be understood that the application area $A_A$ may have any suitable shape or size. The application unit 201 may for example be arranged with a set of spray nozzles for applying the liquid composition C onto the surface S of the cellulose blank structure 2 in the application area $A_A$. In the embodiment illustrated in FIGS. 3a-b, the liquid composition is applied from above the cellulose blank structure 2 onto a first surface S1 of the cellulose blank structure 2 with four spray nozzles arranged in two rows forming the application unit 201. However, any suitable number of spray nozzles may be used. The spray nozzles may be of any suitable construction for distributing the liquid composition C under hydraulic or pneumatic pressure. The arrangement of spray nozzles may differ from the ones described and illustrated, depending on the configuration, shape, and size of the cellulose blank structure 2.

The spray nozzles of the application unit 201 may spray the liquid composition C continuously or intermittently onto the cellulose blank structure 2. The liquid composition may also be applied over the whole cellulose blank structure 2 or only on parts or zones of the cellulose blank structure 2. The spray nozzles may suitably be arranged in a non-illustrated spray booth or similar structure, preventing that the liquid composition C when sprayed are spread into the surrounding environment.

It should be understood that the liquid composition C could be applied onto the cellulose blank structure 2 in two or more sub-steps, and that the same or different types of compositions are applied in the different sub-steps. In the embodiment illustrated in FIGS. 3a-b, a first row of spray nozzles 201a may be used for spraying a first part C1 of the liquid composition C onto the cellulose blank structure 2 and a second row of spray nozzles 201b may be used for spraying a second part C2 of the liquid composition C onto the cellulose blank structure 2. The first part C1 and the second part C2 are together forming the liquid composition C applied to the cellulose blank structure 2. In FIGS. 3a-b, the first part C1 is applied upstream the second part C2, and thus the second part C2 is applied on top of the first part C1. The first part C1 and the second part C2 of the liquid composition C may have different temperatures when applied to the cellulose blank structure 2, and by using different temperatures the control unit 102 could when analyzing the detection result $R_D$ to form the analysis result $R_A$ determine if a temperature deviation in the cellulose blank structure 2 is dependent on a faulty application of either the first part C1 or the second part C2 of the liquid composition C. Thus, the first part C1 may have a first temperature T1 and the second part C2 may have a second temperature T2, where the first temperature T1 is different from the second temperature T2.

In the embodiment schematically illustrated in FIGS. 3a-b and 4a-e, the cellulose blank structure 2 with the applied liquid composition C is fed through the detection area $A_D$ in the feeding direction $D_F$. The detection area $A_D$ is in this embodiment divided into four detection sub-areas arranged in connection to each other. A first detection sub-area $A_{D1}$, a second detection sub-area $A_{D2}$, a third detection sub-area $A_{D3}$, and a fourth detection sub-area $A_{D4}$, are together forming the detection area $A_D$ as understood from for example FIG. 3b. The temperature image I of the detection result $R_D$ comprises detected temperatures of the cellulose blank structure 2 in the detection sub-areas $A_{D1}$-$A_{D4}$, and the detected temperatures are when establishing the analysis result $R_A$ transformed into a temperature image I in the same way as in the embodiment described above. The pre-determined analysis result $R_{APD}$ comprises one or more pre-defined temperature values $T_{PD}$ of the detection sub-areas $A_{D1}$-$A_{D4}$, and the pre-defined temperature values $T_{PD}$ are suitably formed as one or more temperature zones, where each temperature zone has a specific temperature range. Thus, the pre-determined analysis result $R_{APD}$ is in this way formed as a reference temperature image $I_{REF}$ comprising one or more temperature zones, in the same way as described in the embodiment above in connection to FIGS. 2a-e. It should be understood that in alternative embodiments, the detection area $A_D$ could be arranged with any suitable number of sub-areas having the same or different sizes, shapes, and configurations.

Figure 4A:
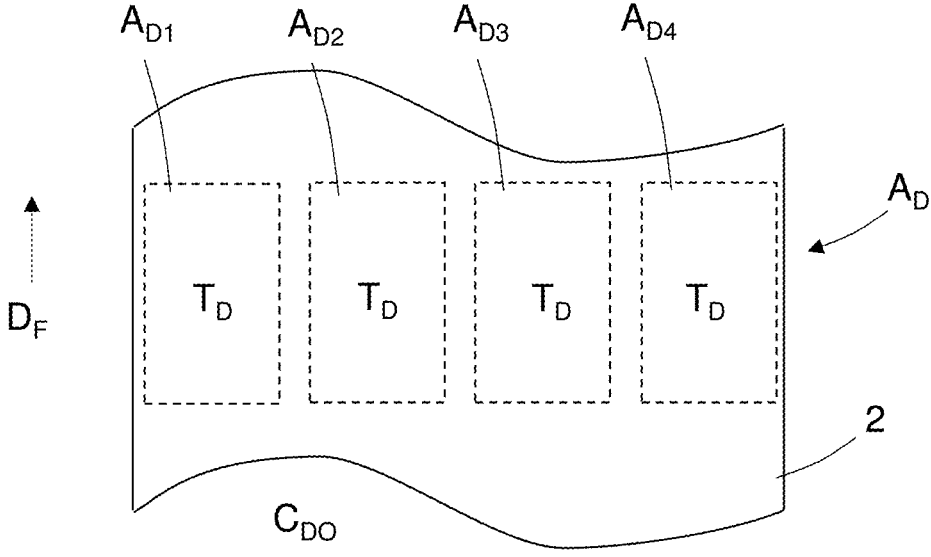
FIG. 4a-e show schematically, in views from above, an alternative embodiment of a detection area of the product forming unit, a reference temperature image, and temperature images of the detection area.

In FIG. 4a, the detection area $A_D$ with the detection sub-areas $A_{D1}$-$A_{D4}$ of the cellulose product forming unit U in the embodiment shown in FIGS. 3a-b is schematically illustrated in a desired operating condition $C_{DO}$. In this embodiment, the liquid composition C is evenly distributed onto the cellulose blank structure 2 in the application area $A_A$ in the desired operating condition $C_{DO}$, which is resulting in an even temperature distribution. In FIG. 4a, a desired temperature value $T_D$ of the cellulose blank structure 2 in the desired operating condition $C_{DO}$ is schematically illustrated for the detection sub-areas $A_{D1}$-$A_{D4}$ and in this embodiment it is assumed that the temperature of the cellulose blank structure 2 with the applied liquid composition C in the detection area $A_D$ has the desired temperature value $T_D$ or essentially the desired temperature value $T_D$, in the same way as described in the embodiment above in connection to FIGS. 2a-e. In FIG. 4c, the reference temperature image $I_{REF}$ with the pre-defined temperature value $T_{PD}$ of the pre-determined analysis result $R_{APD}$ is schematically illustrated. In FIG. 4d, the temperature image I with the desired temperature value $T_D$ of the analysis result $R_A$ in the desired operating condition $C_{DO}$ is schematically illustrated. In this case, the reference temperature image $I_{REF}$ with the pre-defined temperature value $T_{PD}$, as shown in FIG. 4c, is corresponding to the temperature image I with the desired temperature value $T_D$ in the desired operating condition $C_{DO}$, as shown in FIG. 4d. Thus, in the desired operating conditions $C_{DO}$, the desired temperature value $T_D$ and the pre-defined temperature value $T_{PD}$ are the same or essentially the same, and the analysis result $R_A$ in the form of the temperature image I of the detection area $A_D$ based on the detection result $R_D$ is corresponding to the reference temperature image $I_{REF}$. In the desired operating condition $C_{DO}$, the analysis result $R_A$ is not deviating from the pre-determined analysis result $R_{APD}$, and no control action CA is therefore initiated.

Figure 4B:
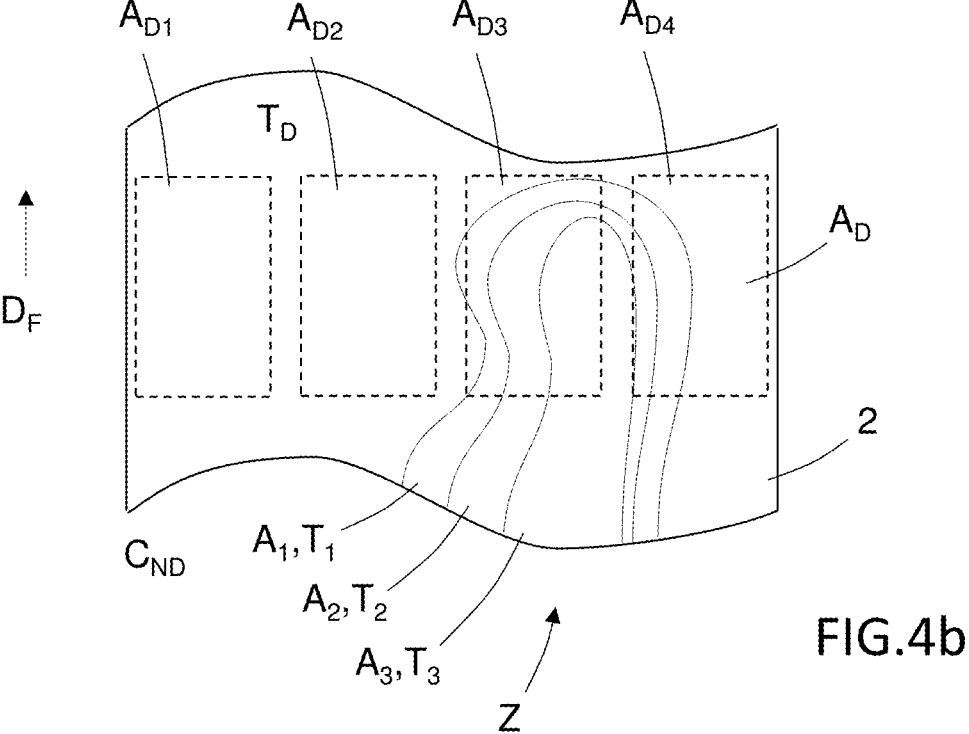
Figures 4C, 4D, 4E:
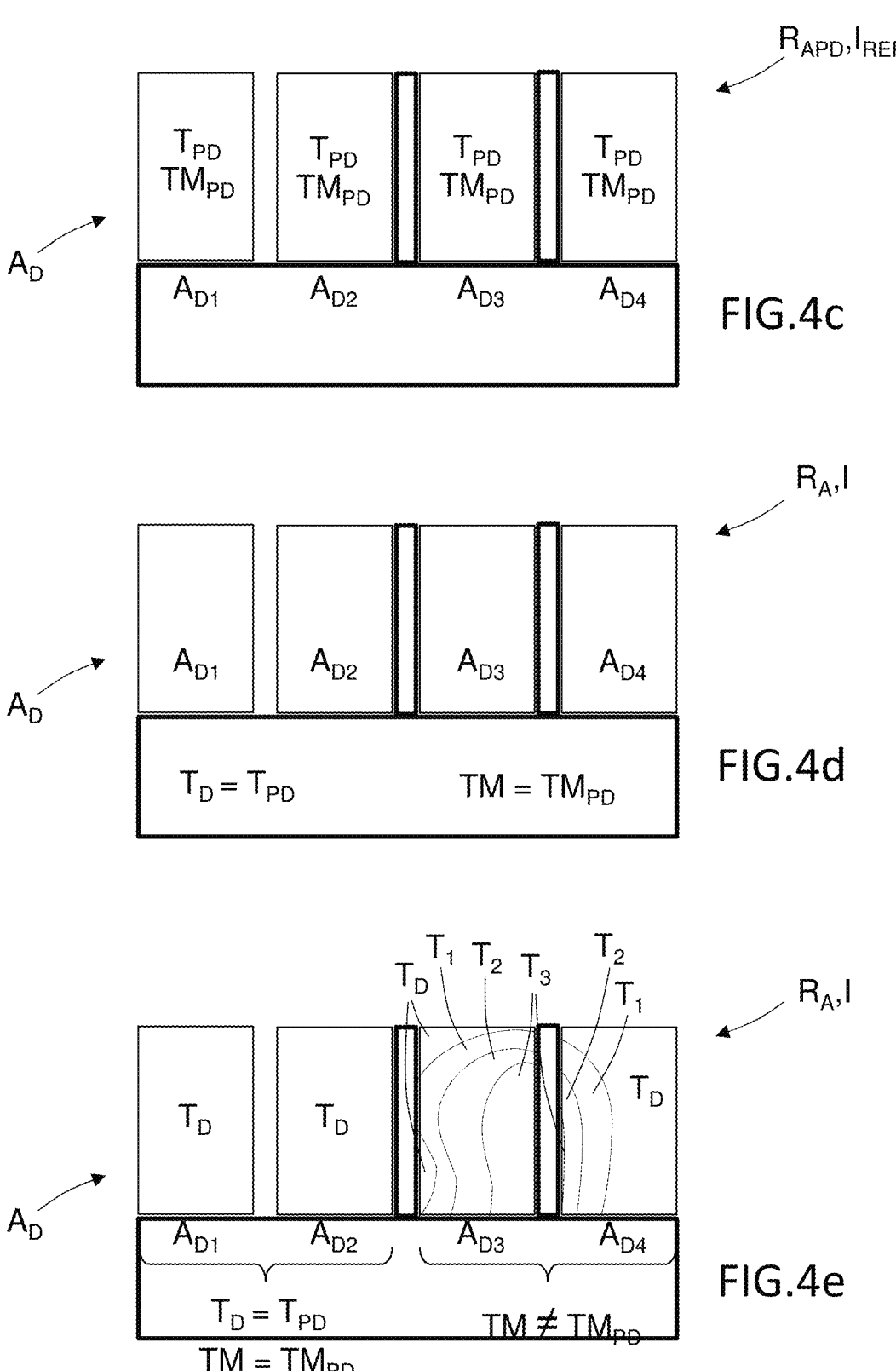

In FIG. 4b, the detection area $A_D$ of the cellulose product forming unit U in the embodiment shown in FIGS. 3a-b is schematically illustrated in a non-desired operating condition $C_{ND}$. In the non-desired operating condition $C_{ND}$, the liquid composition C is unevenly distributed onto the cellulose blank structure 2 in the application area $A_A$, in the same way as described in the embodiment above, and as schematically shown in FIG. 4b, the temperature zone Z comprises a first area A, with a first deviating temperature or temperature range $T_1$, a second area $A_2$ with a second deviating temperature or temperature range $T_2$, and a third area $A_3$ with a third deviating temperature or temperature range $T_3$, and where the part of the cellulose blank structure 2 outside the temperature zone Z is having the desired temperature value $T_D$ as indicated in FIG. 4b.

In FIG. 4e, the temperature image I with the temperature values of the analysis result $R_A$ in the non-desired operating condition $C_{ND}$ is schematically illustrated. As schematically shown in FIG. 4e, parts of the temperature image I, corresponding to the first detection sub-area $A_{D1}$ and the second detection sub-area $A_{D2}$, have the desired temperature value $T_D$. As schematically shown in FIG. 4e, the third detection sub-area $A_{D3}$ and the fourth detection sub-area $A_{D4}$ of the temperature image I each comprises a deviating first temperature or temperature range $T_1$, a deviating second temperature or temperature range $T_2$, and a deviating third temperature or temperature range $T_3$. The deviating temperatures or temperature ranges are higher and/or lower than the desired temperature value $P_D$. In this case, the reference temperature image $I_{REF}$ with the pre-defined temperature value $T_{PD}$, as shown in FIG. 4c, is deviating from the temperature image I in the non-desired operating condition $C_{ND}$, as shown in FIG. 4e. Thus, in the non-desired operating conditions $C_{ND}$, some of the temperature values of the analysis result $R_A$ and the pre-defined temperature value $T_{PD}$ of the pre-determined analysis result $R_{APD}$ are not the same or essentially the same, and the analysis result $R_A$ in the form of the temperature image I of the detection area $A_D$ based on the detection result $R_D$ is not corresponding to the reference temperature image $I_{REF}$. In the non-desired operating condition $C_{ND}$, the analysis result $R_A$ is deviating from the pre-determined analysis result $R_{APD}$, and the control action CA is therefore initiated.

In a similar way as described in the embodiment above in connection to FIGS. 2a-e, the control action CA may be initiated by the control unit 102 when the analysis result $R_A$ is a temperature value T in any part of a detection sub-area $A_{D1}$-$A_{D4}$ different from the pre-defined temperature value $T_{PD}$, or alternatively, when the analysis result $R_A$ is a mean temperature value TM of a detection sub-area $A_{D1}$-$A_{D4}$ different from the pre-defined mean temperature value $TM_{PD}$.

It should be understood that for all embodiments, the reference temperature image $I_{REF}$ could instead comprise two or more temperature values for different parts of the detection area $A_D$. The control action may be arranged in the different ways described above. With the configuration of the detection area $A_D$ comprising detection sub-areas, it is possible to only stop one or more forming molds 3 corresponding to the detection sub-area as the control action CA, where forming molds 3 corresponding to one or more detection sub-areas with deviating temperature values are stopped.

Figure 5:
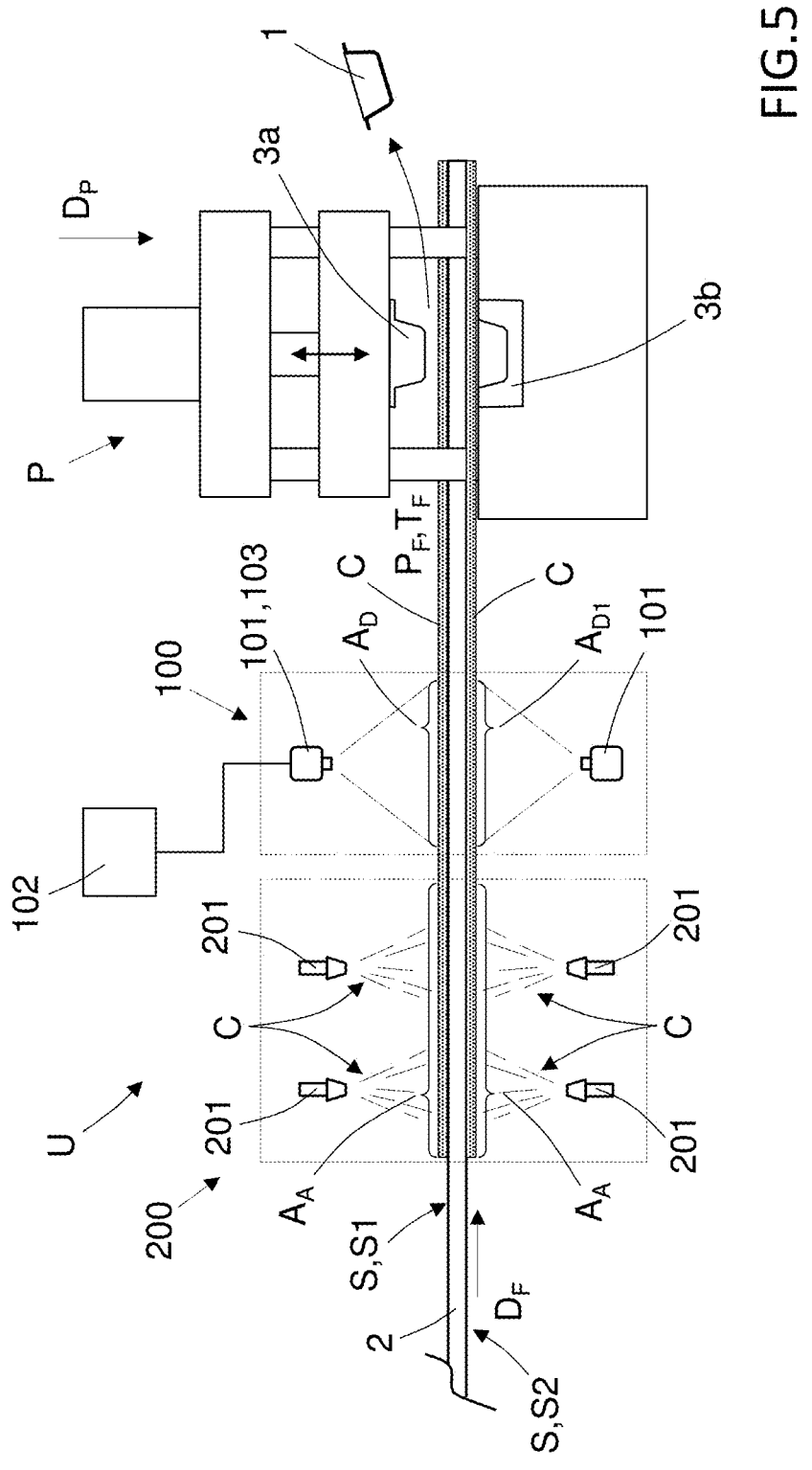
FIG. 5 shows schematically, in a side view, a further alternative embodiment of a cellulose product forming unit, where the cellulose product forming unit comprises a detection system and an application system.

A further alternative embodiment of the product forming unit U is schematically illustrated in FIG. 5. In this alternative embodiment, the detection system 100 and application system 200 are having different configurations compared to the product forming unit U shown in FIGS. 1a-b and 3a-b. The pressing module P may have the same configuration as the pressing module described above in connection to FIGS. 1a-b.

As illustrated in FIG. 5, the liquid composition C is applied to surfaces S of the cellulose blank structure 2 by the application unit 201 of the application system 200. The application unit 201 may for example be arranged with an upper and a lower set of spray nozzles for applying the liquid composition C onto the surfaces S of the cellulose blank structure 2. In the embodiment illustrated in FIG. 5, the liquid composition is applied from above the cellulose blank structure 2 onto a first surface S1 of the cellulose blank structure 2 in an upper application area $A_A$ with two spray nozzles, and onto a second surface S2 in a lower application area $A_A$ with two spray nozzles, where the four spray nozzles together are forming the application unit 201. As understood from FIG. 5, the liquid composition C is applied to the cellulose blank structure 2 in the application areas $A_A$. The application areas $A_A$ are in this embodiment defining an upper area and a lower area of the product forming unit U through which the cellulose blank structure 2 is fed in the feeding direction $D_F$. The liquid composition C is thus applied onto the cellulose blank structure 2 in the application areas $A_A$ upon transportation of the cellulose blank structure 2 in the feeding direction $D_F$, and the application areas $A_A$ may have any suitable extension in the feeding direction $D_F$ and in a direction perpendicular to the feeding direction $D_F$. The application areas $A_A$ may have any suitable shapes or sizes. Any suitable number of spray nozzles may be used for applying the liquid composition C onto the cellulose blank structure 2. The spray nozzles may be of any suitable construction for distributing the liquid composition C under hydraulic or pneumatic pressure. The arrangement of spray nozzles may differ from the ones described and illustrated, depending on the configuration, shape, and size of the cellulose blank structure 2. In the illustrated embodiment, the first surface S1 is an upper surface of the cellulose blank structure 2 and the second surface S2 is an opposite lower surface of the cellulose blank structure 2. In this embodiment, the liquid composition C is applied to both the upper surface and the lower surface of the cellulose blank structure 2. It should be understood that the liquid composition C applied to the first surface S1 and the second surface S2 may have the same chemical composition, or alternatively, a liquid composition C applied to the first surface S1 may have a chemical composition different from a liquid composition C applied to the second surface S2. Also in this embodiment, the liquid composition C could be applied onto cellulose blank structure 2 in two or more sub-steps in the same way as described above in connection to FIGS. 3a-b.

The spray nozzles of the application unit 201 may spray the liquid composition C continuously or intermittently onto the cellulose blank structure 2. The liquid composition may also be applied over the whole cellulose blank structure 2 or only on parts or zones of the cellulose blank structure 2. The spray nozzles may suitably be arranged in a non-illustrated spray booth or similar structure, preventing that the liquid composition C when sprayed are spread into the surrounding environment.

In the embodiment illustrated in FIG. 5, the detection system 100 comprises two detection units 101 arranged on each side of the cellulose blank structure 2. Each detection unit 101 is arranged in connection to a corresponding detection area $A_D$ of the product forming unit U, and the detection units 101 are used for detecting if the liquid composition C has been applied correctly on both sides of the cellulose blank structure. Each detection area $A_D$ may have the same configurations as described in any of the different embodiments above, with the same control actions CA.

It should be understood that the cellulose product forming unit U may be configured in other ways. As an example, two or more detection units 101 or rows of detection units 101 may be used for detecting the liquid composition C. If the liquid composition C is applied onto the cellulose blank structure 2 in two or more sub-steps, a detection unit 101 or row of detection units 101 may be arranged after each sub-step or after a specific number of sub-steps. The detection results $R_D$ from the detection units 101 are distributed to the control unit 102 for further analysis to form the analysis result $R_A$. The analysis result $R_A$ may be arranged as a plurality of temperature images I that are compared to a plurality of reference temperature images $I_{REF}$.

Figure 6:
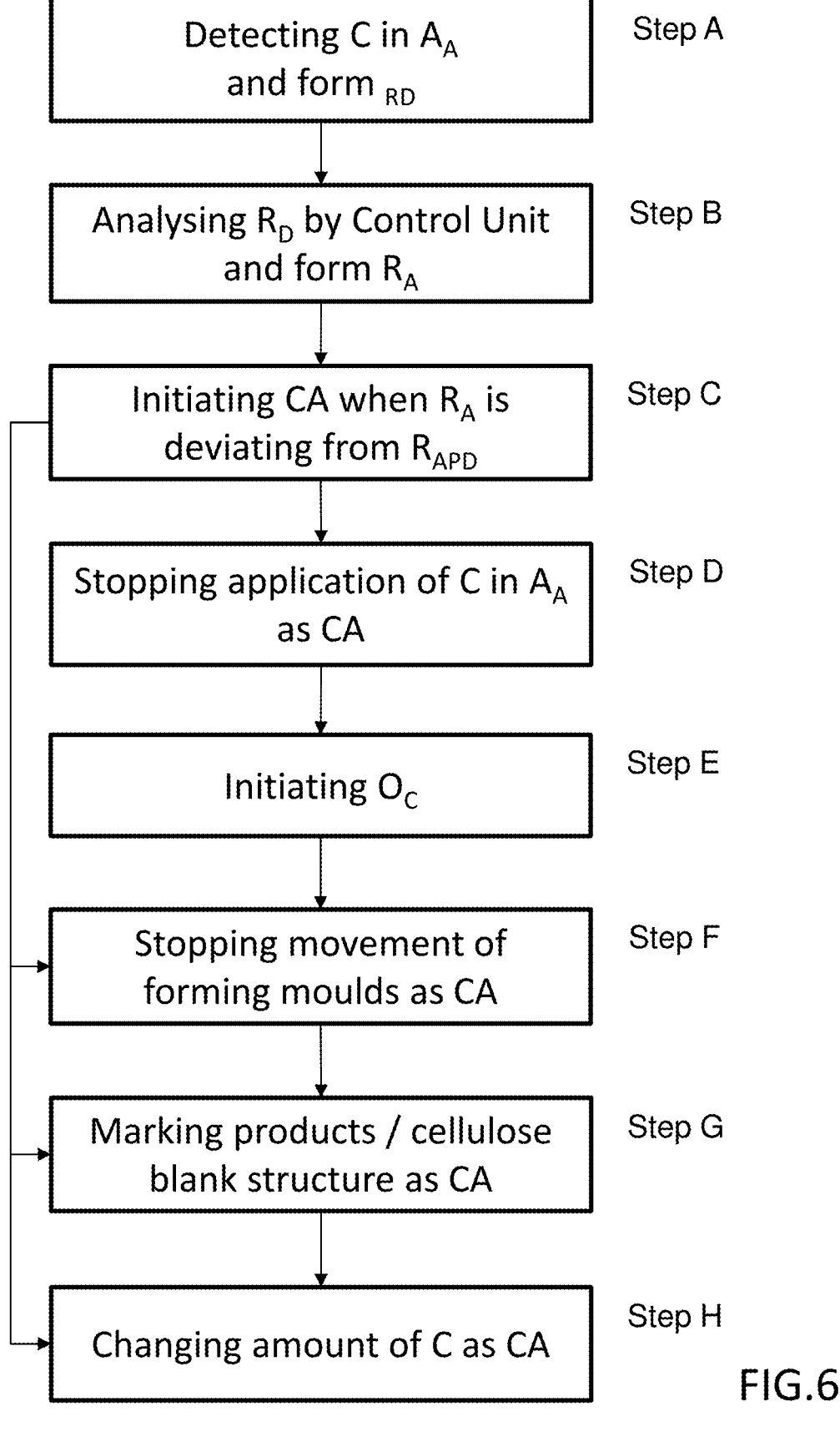
FIG. 6 shows schematically, a flowchart of exemplified method steps for detecting a liquid composition applied onto a cellulose blank structure.

A flowchart of an exemplified method for detecting a liquid composition C applied onto a cellulose blank structure 2 is shown in FIG. 6. The exemplified method comprises the steps described below with reference to FIG. 6.

In step A, the applied liquid composition C is detected in the detection area $A_D$ with the detection unit 101, and the detection by the detection unit 101 is forming a detection result $R_D$.

In step B, the detection result $R_D$ is analyzed by the control unit 102, and the analysis of the detection result $R_D$ is forming an analysis result $R_A$.

In step C, a control action CA is initiated by the control unit 102 upon detection of an analysis result $R_A$ deviating from a pre-determined analysis result $R_{APD}$.

In step D, the application of the liquid composition C onto the cellulose blank structure 2 by the application unit 201 in the application area $A_A$ is stopped as the control action CA.

In step E, a cleaning operation $O_C$ of the application unit 201 is initiated after stopping the application of the liquid composition C onto the cellulose blank structure 2 by the application unit 201.

In step F, a movement of the one or more forming molds 3 is stopped as the control action CA.

In step G, one or more cellulose products 1 and/or the cellulose blank structure 2 are marked as the control action CA.

In step H, the amount of liquid composition C applied onto the cellulose blank structure in the application area $A_A$ is changed as the control action CA.

According to the method, one or more control actions may be initiated upon detection of an analysis result $R_A$ deviating from a pre-determined analysis result $R_{APD}$.

The present disclosure has been presented above with reference to specific embodiments. However, other embodiments than the above described are possible and within the scope of the disclosure. Different method steps than those described above, performing the method by hardware or software, may be provided within the scope of the disclosure. Thus, according to an exemplary embodiment, there is provided a non-transitory computer-readable storage medium storing one or more programs configured to be executed by one or more processors of the control unit, the one or more programs comprising instructions for performing the method according to any one of the above-discussed embodiments. Alternatively, according to another exemplary embodiment a cloud computing system can be configured to perform any of the method aspects presented herein. The cloud computing system may comprise distributed cloud computing resources that jointly perform the method aspects presented herein under control of one or more computer program products. Moreover, the processor may be connected to one or more communication interfaces and/or sensor interfaces for receiving and/transmitting data with external entities such as e.g. sensors, an off-site server, or a cloud-based server.

The processor or processors associated with the control may be or include any number of hardware components for conducting data or signal processing or for executing computer code stored in memory. The system may have an associated memory, and the memory may be one or more devices for storing data and/or computer code for completing or facilitating the various methods described in the present description. The memory may include volatile memory or non-volatile memory. The memory may include database components, object code components, script components, or any other type of information structure for supporting the various activities of the present description. According to an exemplary embodiment, any distributed or local memory device may be utilized with the systems and methods of this description. According to an exemplary embodiment the memory is communicably connected to the processor (e.g., via a circuit or any other wired, wireless, or network connection) and includes computer code for executing one or more processes described herein.

It will be appreciated that the above description is merely exemplary in nature and is not intended to limit the present disclosure, its application or uses. While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out the teachings of the present disclosure, but that the scope of the present disclosure will include any embodiments falling within the foregoing description and the appended claims. Reference signs mentioned in the claims should not be seen as limiting the extent of the matter protected by the claims, and their sole function is to make claims easier to understand.

The invention claimed is:

1. A method for detecting a liquid composition applied onto a fluffy cellulose blank structure, with a detection system, wherein the detection system is part of a cellulose product forming unit for forming non-flat cellulose products from the fluffy cellulose blank structure, wherein the detection system comprises a detection unit comprising an infrared thermal detection sensor connected to a control unit, the method comprising the steps of:

providing the fluffy cellulose blank structure and feeding the fluffy cellulose blank structure in a feeding direction, wherein the fluffy cellulose blank structure upon feeding is moving through an application area comprising at least one spray nozzle and a detection area, wherein the application area is arranged upstream of the detection area;

spraying the liquid composition onto the fluffy cellulose blank structure in the application area with the at least one spray nozzle;

detecting the applied liquid composition in the detection area with the detection unit, wherein the detection by the detection unit includes forming a detection result, wherein the detection result is a temperature image of the detection area;

analyzing the temperature image by the control unit, wherein the analysis of the temperature image includes forming an analysis result; and initiating a control action by the control unit upon detection of an analysis result deviating from a pre-determined analysis result.

2. The method according to claim 1, wherein the analysis result comprises temperature values of the detection area and wherein the pre-determined analysis result comprises pre-defined temperature values, wherein the method further comprises the step of: initiating the control action by the control unit when the analysis result is a temperature value in any part of the detection area above or below the pre-defined temperature values.

3. The method according to claim 1, wherein the analysis result comprises a mean temperature value of the detection area and wherein the pre-determined analysis result is a pre-defined mean temperature value, wherein the method further comprises the step of: initiating the control action by the control unit when the analysis result is a mean temperature value above or below the pre-defined mean temperature value.

4. The method according to claim 1, wherein the method further comprises the step of: continuously detecting the applied liquid composition in the detection area by the detection unit.

5. The method according to claim 1, wherein the method further comprises the step of: intermittently detecting the applied liquid composition in the detection area by the detection unit.

6. The method according to claim 1, wherein the liquid composition is applied onto the cellulose blank structure in the application area by the at least one spray nozzle, wherein the method further comprises the step of: stopping the application of the liquid composition onto the cellulose blank structure by the at least one spray nozzle in the application area as the control action.

7. The method according to claim 6, wherein the method further comprises the step of: initiating a cleaning operation of the at least one spray nozzle after stopping the application of the liquid composition onto the cellulose blank structure by the at least one spray nozzle.

8. The method according to claim 1, wherein the cellulose product forming unit comprises one or more forming molds for forming non-flat cellulose products, wherein the method further comprises the steps of: stopping a movement of the one or more forming molds as the control action.

9. The method according to claim 1, wherein the method further comprises the steps of: marking one or more cellulose products and/or the cellulose blank structure as the control action.

10. The method according to claim 1, wherein the method further comprises the steps of: removing one or more cellulose products and/or the cellulose blank structure as the control action.

11. The method according to claim 1, wherein the method further comprises the steps of: changing the amount of liquid composition applied onto the cellulose blank structure in the application area as the control action.

12. The method according to claim 1, wherein the method further comprises the steps of: applying the liquid composition onto the cellulose blank structure in two or more sub-steps, wherein in each sub-step a part of the liquid composition is applied onto the cellulose blank structure.

13. The method according to claim 12, wherein a temperature of each part of the liquid composition is different from the other parts.

14. A detection system for detecting a liquid composition applied onto a fluffy cellulose blank structure upon feeding the fluffy cellulose blank structure in a feeding direction through an application area and a detection area, wherein the detection system forms part of a cellulose product forming unit for forming non-flat cellulose products from the fluffy cellulose blank structure, the detection system comprising:

a detection unit comprising an infrared thermal detection sensor connected to a control unit, wherein the detection unit is configured for detecting the applied liquid composition in the detection area arranged downstream an application area in which the liquid composition is applied onto the fluffy cellulose blank structure by at least one spray nozzle, wherein the detection by the detection unit forms a detection result, wherein the detection result is a temperature image of the detection area;

wherein the control unit is configured to analyze the temperature image, wherein the analysis of the temperature image forms an analysis result, and wherein the control unit is configured for initiating a control action upon detection of an analysis result deviating from a pre-determined analysis result.

* * * * *